(12) United States Patent
Motsenbocker et al.

(10) Patent No.: US 7,069,794 B2
(45) Date of Patent: Jul. 4, 2006

(54) RADIAL EXPANSION FORCE MEASUREMENT TECHNOLOGY

(75) Inventors: Tom Motsenbocker, Flagstaff, AZ (US); Edward Goff, Phoenix, AZ (US)

(73) Assignee: Machine Solutions, Inc., Flagstaff, AZ (US)

( * ) Notice: Subject to any disclaimer, the term of this patent is extended or adjusted under 35 U.S.C. 154(b) by 0 days.

(21) Appl. No.: 10/986,650

(22) Filed: Nov. 10, 2004

(65) Prior Publication Data

US 2005/0115336 A1 Jun. 2, 2005

Related U.S. Application Data

(60) Provisional application No. 60/518,773, filed on Nov. 10, 2003.

(51) Int. Cl.
*G01D 7/00* (2006.01)
(52) U.S. Cl. .................................. 73/862.041
(58) Field of Classification Search ............ 73/862.041
See application file for complete search history.

(56) References Cited

U.S. PATENT DOCUMENTS

| | | | | |
|---|---|---|---|---|
| 4,342,225 | A * | 8/1982 | Jandera et al. | 73/865.8 |
| 5,056,384 | A * | 10/1991 | Sergan | 81/57.39 |
| 5,088,336 | A * | 2/1992 | Rosenberg et al. | 73/865.8 |
| 5,695,504 | A * | 12/1997 | Gifford et al. | 606/153 |
| 5,948,173 | A * | 9/1999 | Huh et al. | 134/34 |
| 6,113,273 | A * | 9/2000 | Eberle et al. | 384/40 |
| 6,475,293 | B1 * | 11/2002 | Moinpour et al. | 134/6 |
| 6,857,330 | B1 * | 2/2005 | Murphy et al. | 73/865.8 |
| 2005/0103121 | A1 * | 5/2005 | Chen et al. | 73/856 |

* cited by examiner

*Primary Examiner*—Max Noori
(74) *Attorney, Agent, or Firm*—Skinner and Associates

(57) ABSTRACT

An apparatus for measuring force, particularly the radial expansion force or hoop force associated with a stent or other article. The apparatus includes an article engagement mechanism. The article engaging mechanism includes at least one stationary plate member; at least one rotatable force collector member which is moveable in relation to the stationary member, and a plurality of force element segments, each having a predetermined wedge shape with a proximal end and a distal end. Each segment also has a distal point which is pivotally coupled to the stationary plate member and a proximal point which is pivotally coupled to the rotatable force collector member. The segments are arranged so that the segment distal ends are disposed adjacent a central aperture into which the article is placed. The segment distal ends move to engage the article upon rotation of the rotatable member in a predetermined direction. The apparatus further includes an actuator for rotating the rotatable force collector member; and a transducer communicatively connected to the actuator for detecting force associated with rotating the rotatable member, and hence the force elements to engage the article. A method of detecting force associated with an article is also disclosed. The method includes the steps of providing an article engagement mechanism having a design of the apparatus. An article is placed in the central aperture. An engaging force is applied to the article with the distal ends of the segments by rotating the force collector. The force required to rotate the force collector, and hence move the force elements against the article is used as a measure of radial expansion force of the article.

26 Claims, 31 Drawing Sheets

RADIAL EXPANSION FORCE MEASUREMENT TECHNOLOGY

CROSS-REFERENCE TO RELATED APPLICATIONS, IF ANY

This application claims the benefit under 35 U.S.C. §119(e) of U.S. Provisional Patent Application Ser. No. 60/518,773, filed Nov. 10, 2003 now abandoned, which is hereby incorporated by reference.

37 C.F.R. §1.71(e) AUTHORIZATION

A portion of the disclosure of this patent document contains material which is subject to copyright protection. The copyright owner has no objection to the facsimile reproduction by anyone of the patent document or the patent disclosure, as it appears in the US Patent and Trademark Office patent file or records, but otherwise reserves all copyright rights whatsoever.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND OF THE INVENTION

1. Field of the Invention

The present invention relates, generally, to measurement apparatus and methods. Particularly, the invention relates to radial expansion force measurement apparatus and methods. Most particularly, the invention relates to an apparatus and method of measuring the radial expansion force which would be exerted by a balloon expandable or self expanding stent, stent graft, or similar medical device on the vasculature, which is also known as hoop force. The teachings of this invention are also applicable to other apparatus, methods and applications, including but not limited to catheters, balloons, tubes, conduits, filters, and the like whether in the medical field or other fields.

2. Background Information

Various medical procedures exist which involve inserting devices into the vasculature of a patient. These include endoscopy, biopsy, angiography, angioplasty, atherectomy, and the like. Percutaneous transluminal coronary angioplasty (PTCA) is a form of angioplasty which is performed to reduce or eliminate blockages in coronary arteries and restore or improve blood to flow heart tissue. Arteries are accessed by advancing a catheter through a percutaneous needle puncture made in the groin to the femoral artery, or arm to the brachial artery. A balloon disposed on the catheter is placed to opening a blockage caused by plaque in a coronary artery and inflated to open the blockage. A stent is a tubular structure, which may be drug coated, may be implanted at the blockage site via a catheter after angioplasty to keep the artery open and prevent regrowth of plaque or restenosis.

Hoop strength is a physical property that describes the ability of a tube to withstand internal pressure, bending and crushing forces. Hoop strength is an important characteristic of stents.

The state of the art includes various apparatus and methods of measuring force, in general. With respect to hoop force measurement, U.S. Pat. No. 6,568,235 to Kokish on May 27, 2003 entitled Assembly for Crimping an Intraluminal Device or Measuring the Radial Strength of the Intraluminal Device and Method of use discloses an assembly including a stationary disk, a drive disk, wedges uniformly spaced to provide substantially frictionless movement among the wedges, and linear sliders attached to a front face of the stationary disk.

This background technology is believed to have significant limitations and shortcomings. For this and other reasons, a need exists for the present invention.

All US patents and patent applications, and all other published documents mentioned anywhere in this application are incorporated by reference in their entirety.

BRIEF SUMMARY OF THE INVENTION

The invention provides an apparatus and method for measuring radial expansion force which are practical, reliable, accurate and efficient, and which are believed to fulfil the need and to constitute an improvement over the background technology.

In one aspect, the invention provides an apparatus for detecting force associated with an article, comprising:
 (a.) an article engagement mechanism having:
  at least one stationary plate member;
  at least one rotatable force collector member which is moveable in relation to the stationary member;
  a plurality of force element segments, each having a predetermined wedge shape with a proximal end and a distal end, each segment having a distal point and a proximal point, the distal point being pivotally coupled to the stationary member and the proximal point being pivotally movably coupled to the rotatable member;
  the segments being arranged so that the segment distal ends are disposed adjacent a central aperture adapted to receive an article; and
  the segment distal ends moving to engage the article disposed in the central aperture upon rotation of the rotatable member in a predetermined direction;
 (b.) an actuator for rotating the rotatable member; and
 (c.) a transducer communicatively connected to the actuator for detecting force associated with rotating the rotatable member.

In another aspect, the invention provides method of detecting force associated with an article comprising the steps of:
 a. providing an article engagement mechanism having:
  at least one stationary plate member;
  at least one rotatable force collector member which is moveable in relation to the stationary member;
  a plurality of force element segments, each having a proximal end and a distal end, each segment having a distal point and a proximal point, the distal point being pivotally coupled to the stationary member and the proximal point being pivotally movably coupled to the rotatable member;
  the segments being arranged so that the segment distal ends are disposed adjacent a central aperture; and
  the segment distal ends moving to decrease the diameter of the central aperture upon rotation of the rotatable member in a predetermined direction;
 b. placing an article in the central aperture;

c. rotating the rotatable member to apply an engaging force to the article with the distal ends of the segments; and d. measuring the force required to rotate the rotatable member and thus engage the article with the segments, whereby the force is used as a measure of radial expansion force.

The features, benefits and objects of the invention will become clear to those skilled in the art by reference to the following description, claims, and drawings.

DETAILED DESCRIPTION

1. Introduction

Figure 12:
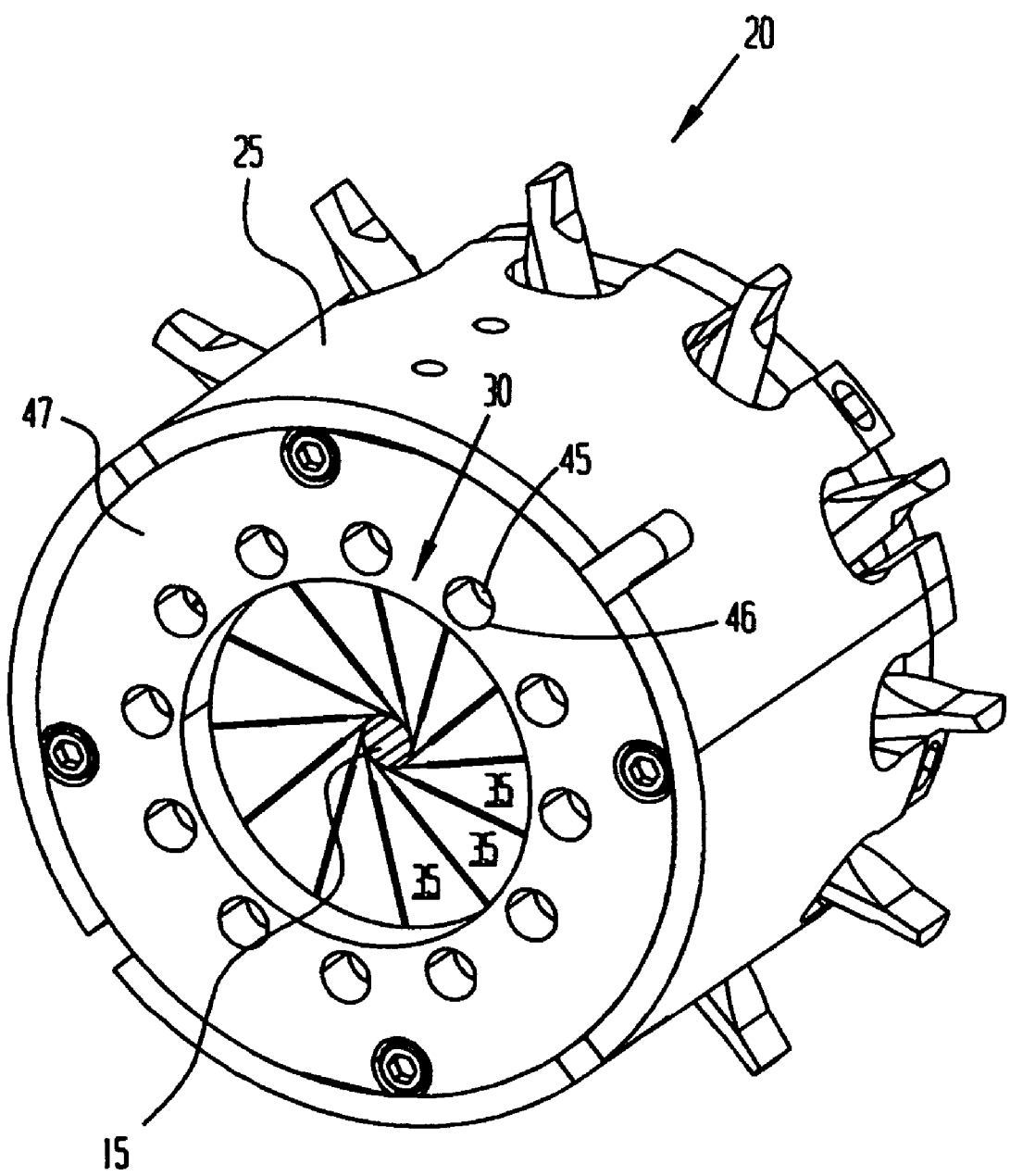
FIG. 12 is a perspective view of a stent in an operative position in the front face of the radial expansion force measurement assembly.
Figure 13:
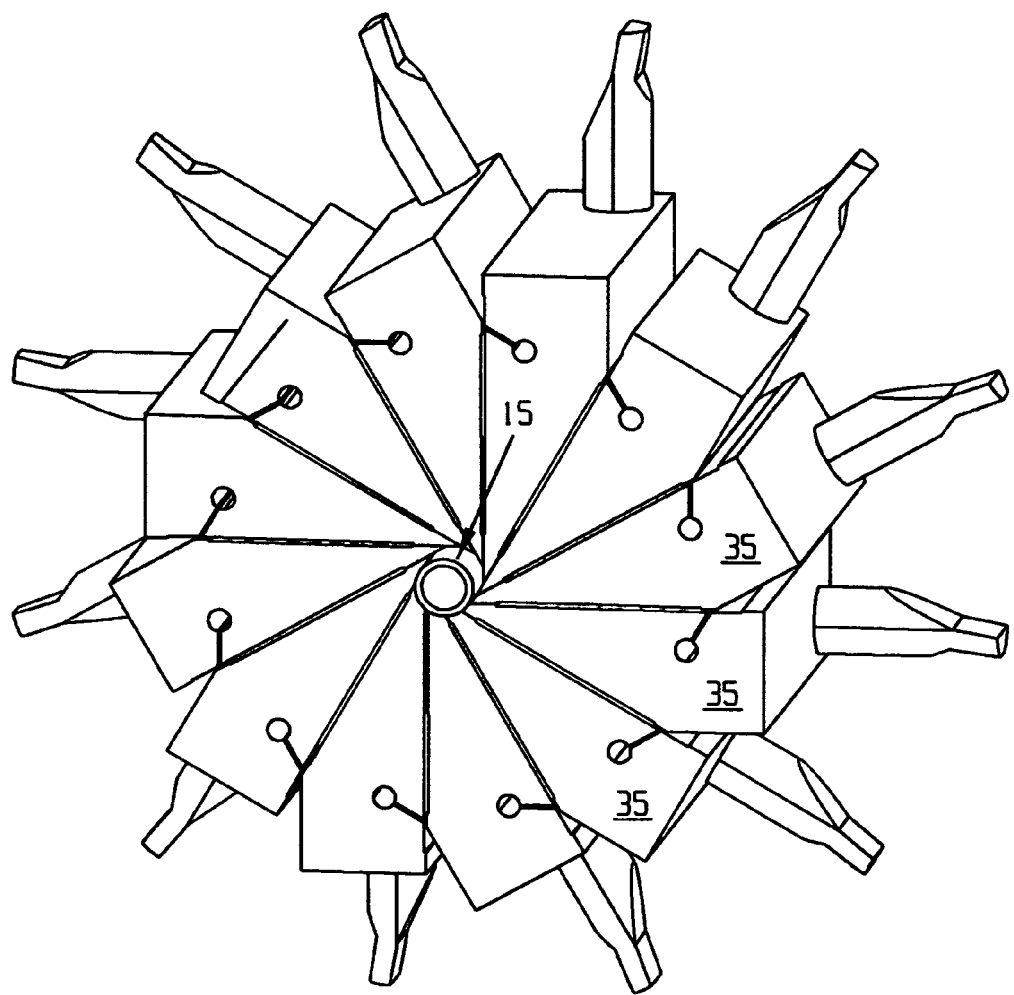
FIG. 13 is a close perspective view of the stent shown in FIG. 12.
Figure 14:
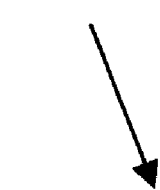
FIG. 14 illustrates an embodiment of the control panel of the embodiment of the radial expansion force measurement system.
Figure 14:
Figure 14:
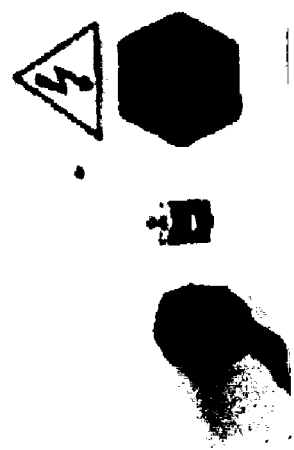

The system, apparatus and method of the present invention uses a segmental radial engagement assembly preferably with a relatively high segment count and low friction to convert hoop force to linear force. The system, apparatus and method are useful for measuring radial expansion force, particularly hoop force, in an article, most particularly a medical stent 15 as shown in FIGS. 12 and 13. The apparatus 11 yields no pinching and low specimen to fixture friction. The apparatus maintains resolution at force levels of 0 to 80 Newtons (N). The system 10, apparatus and method can be used to measure actual hysteresis, hoop strength, and creep.

The commonly-used definition of "hoop force" in a circular-cylindrical-shell-shaped device such as a stent 15 is the total circumferential force transmitted across an imaginary lengthwise cut through the wall of the device. The system 10 of this invention measures the force applied by the specimen 15 to multiple sides of a polygon, then calculates a hoop-force equivalent.

2. System and Apparatus of the Invention

Figure 1:
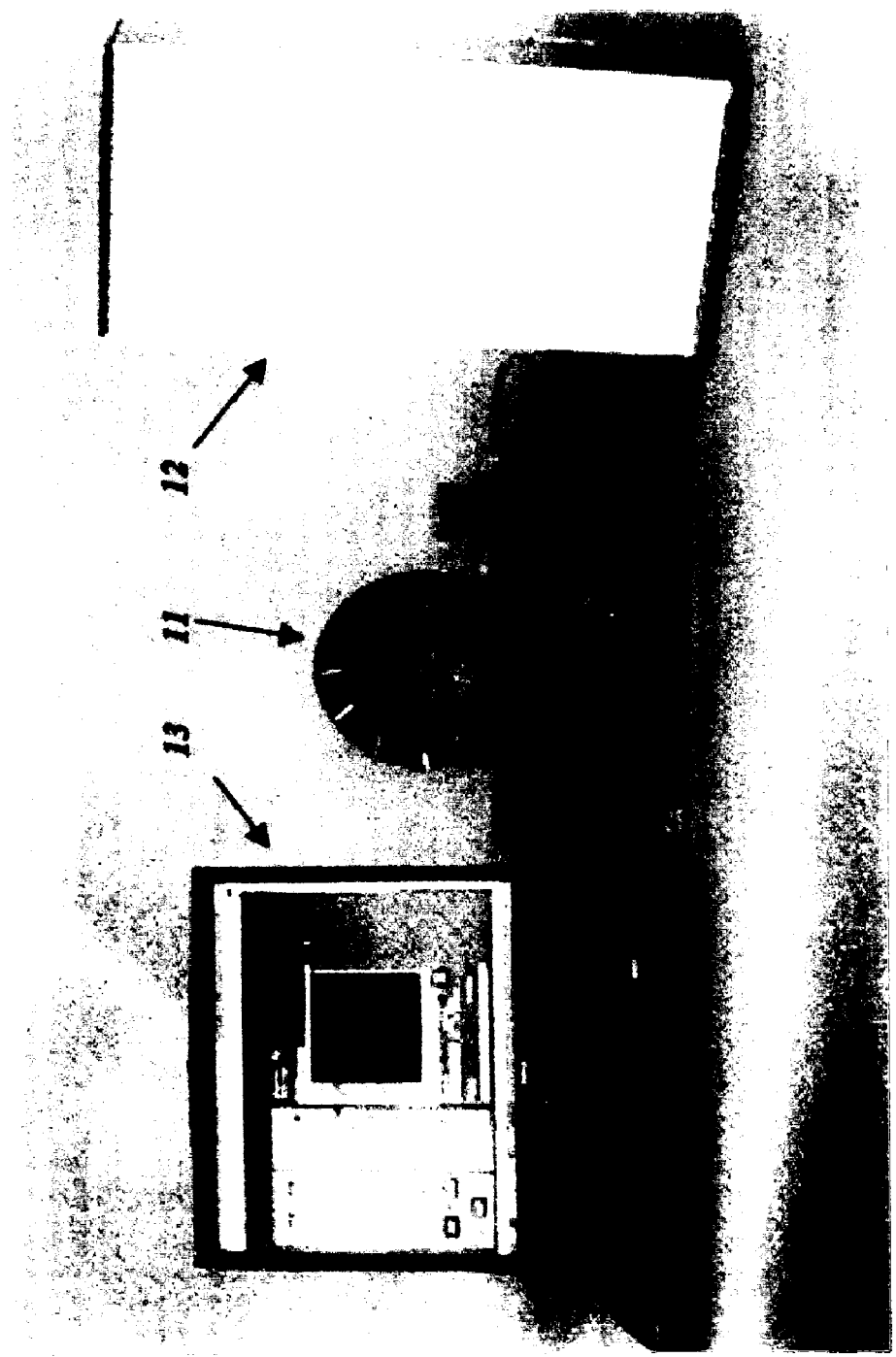
FIG. 1 shows an embodiment of the radial expansion force measurement system of the present invention.
Figure 2A:
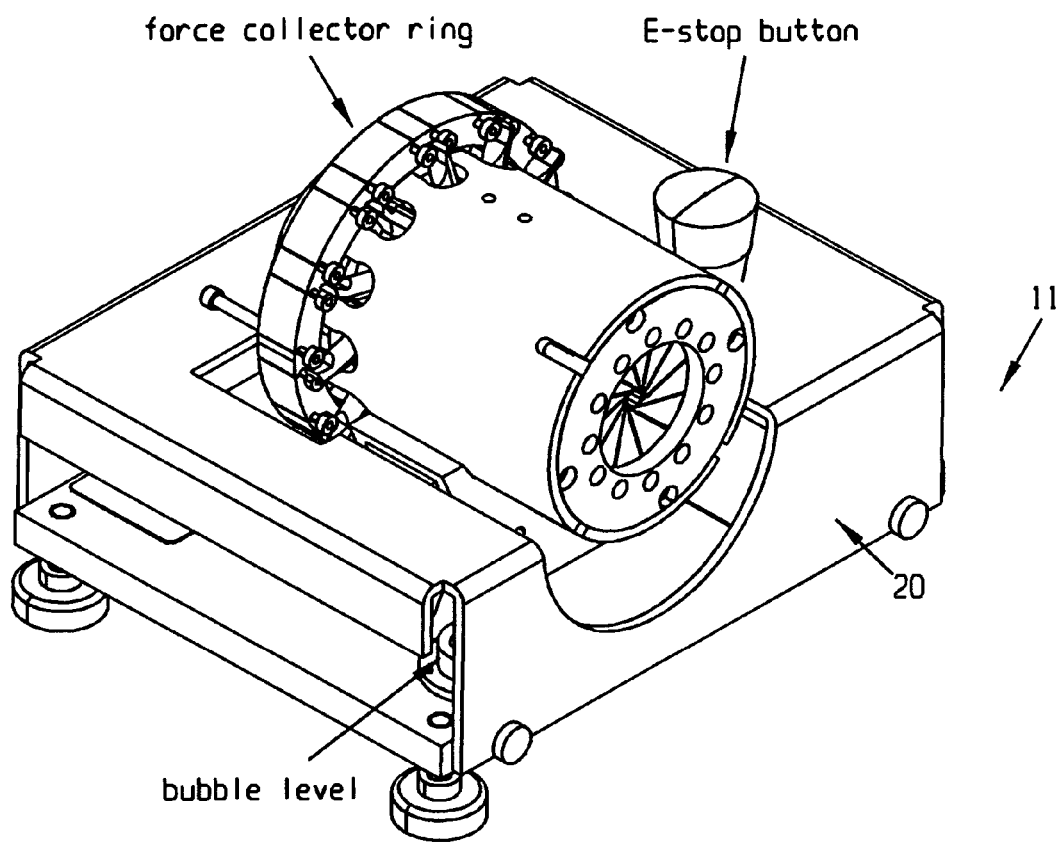
FIGS. 2a/b show a perspective view of an embodiment of the radial expansion force measurement assembly or apparatus, used in the system shown in FIG. 1, of the present invention.
Figure 2B:
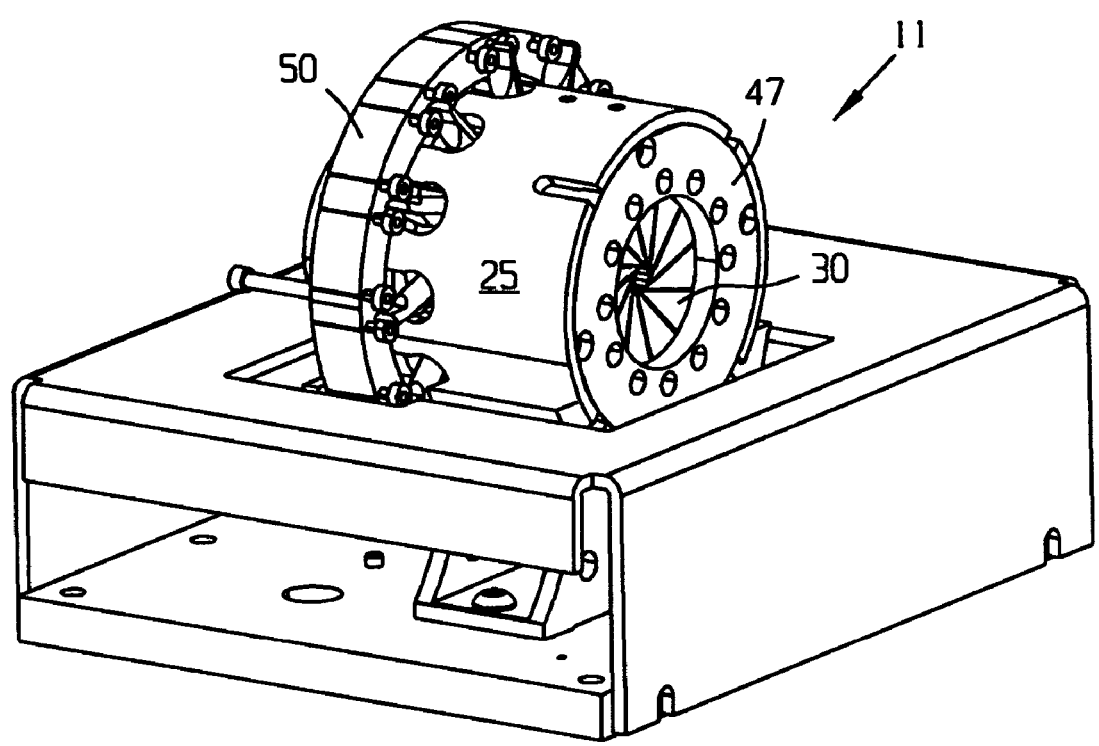
Figure 3A:
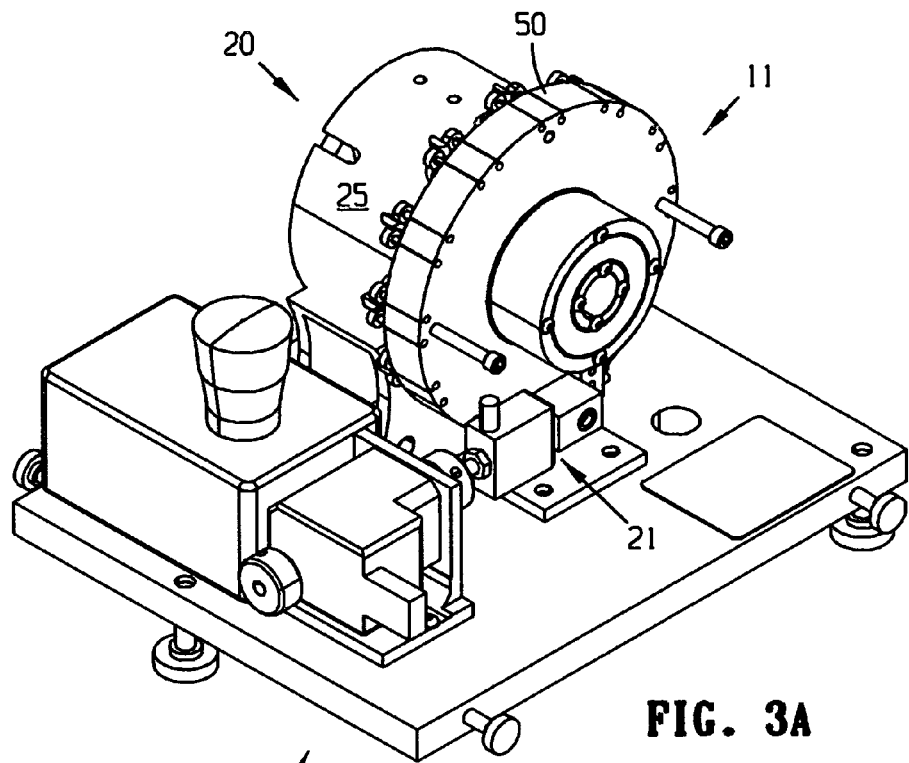
FIGS. 3a/b/c show another perspective view of the assembly.
Figure 3B:
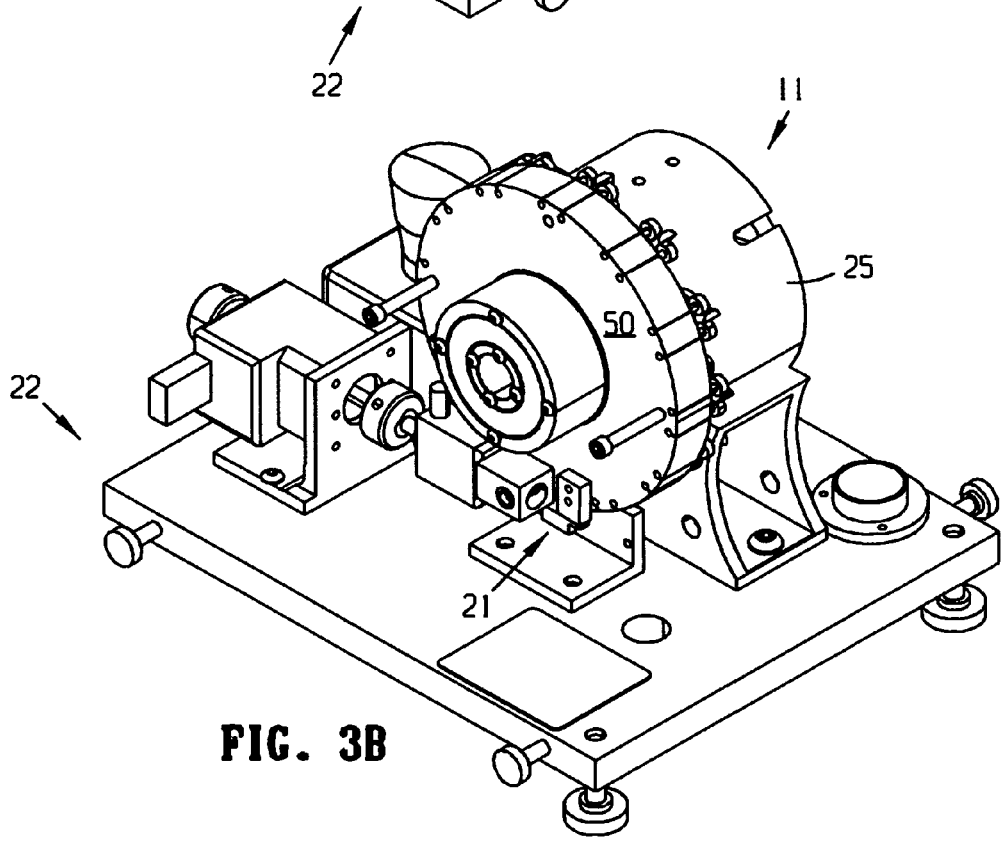
Figure 3C:
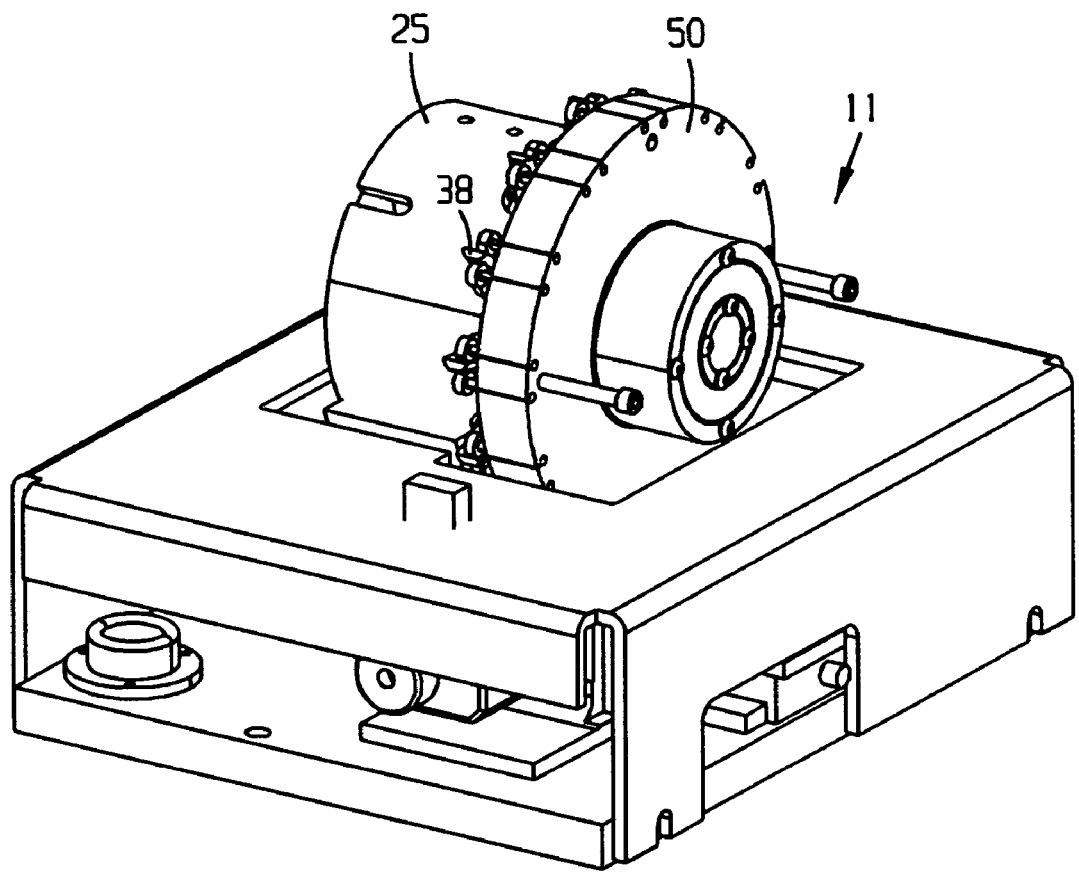
Figure 4:
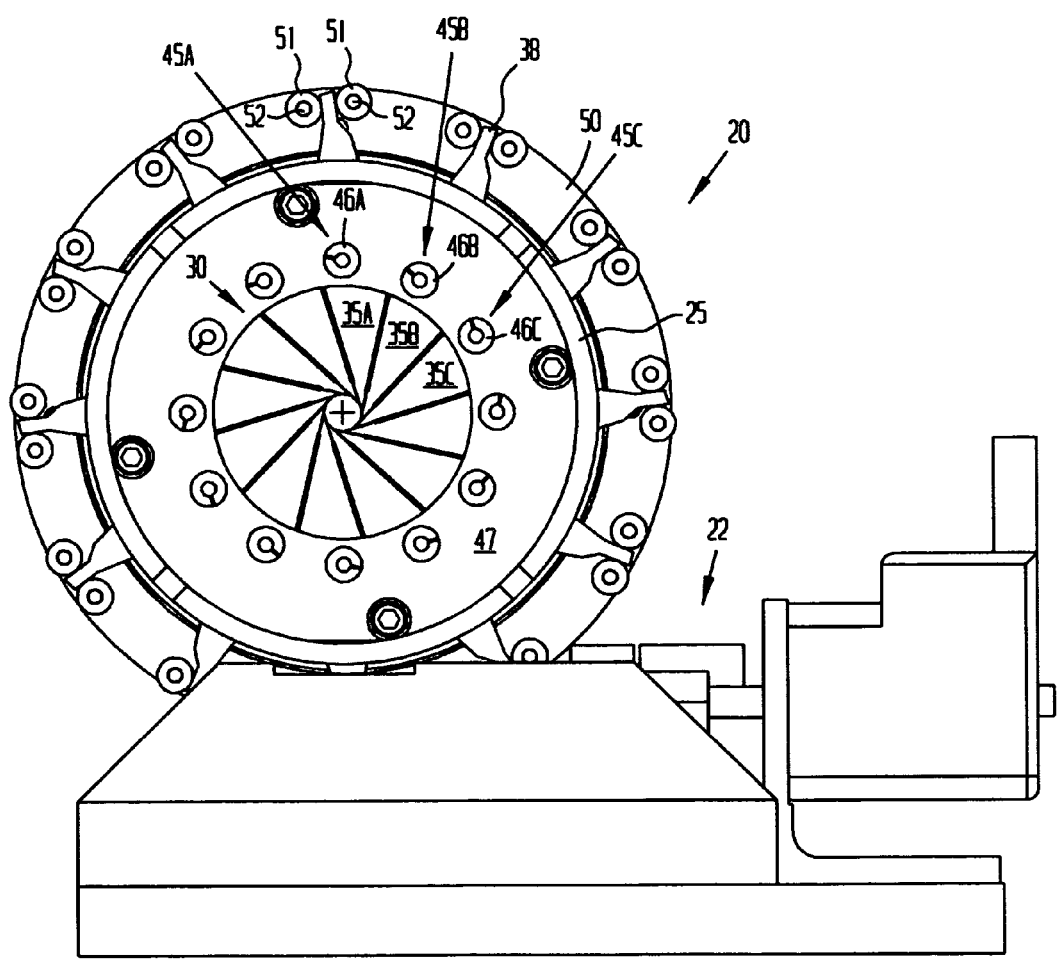
FIG. 4 is a front elevation view of the assembly.
Figure 5:
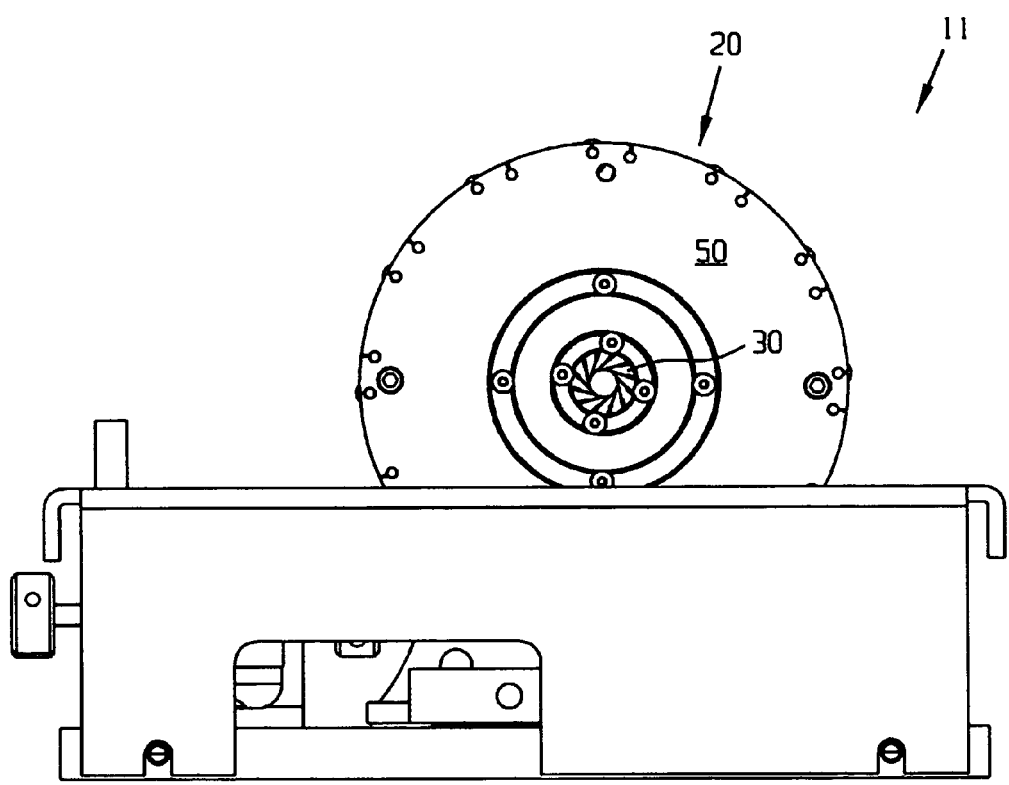
FIG. 5 is a back view of the assembly.
Figure 6A:
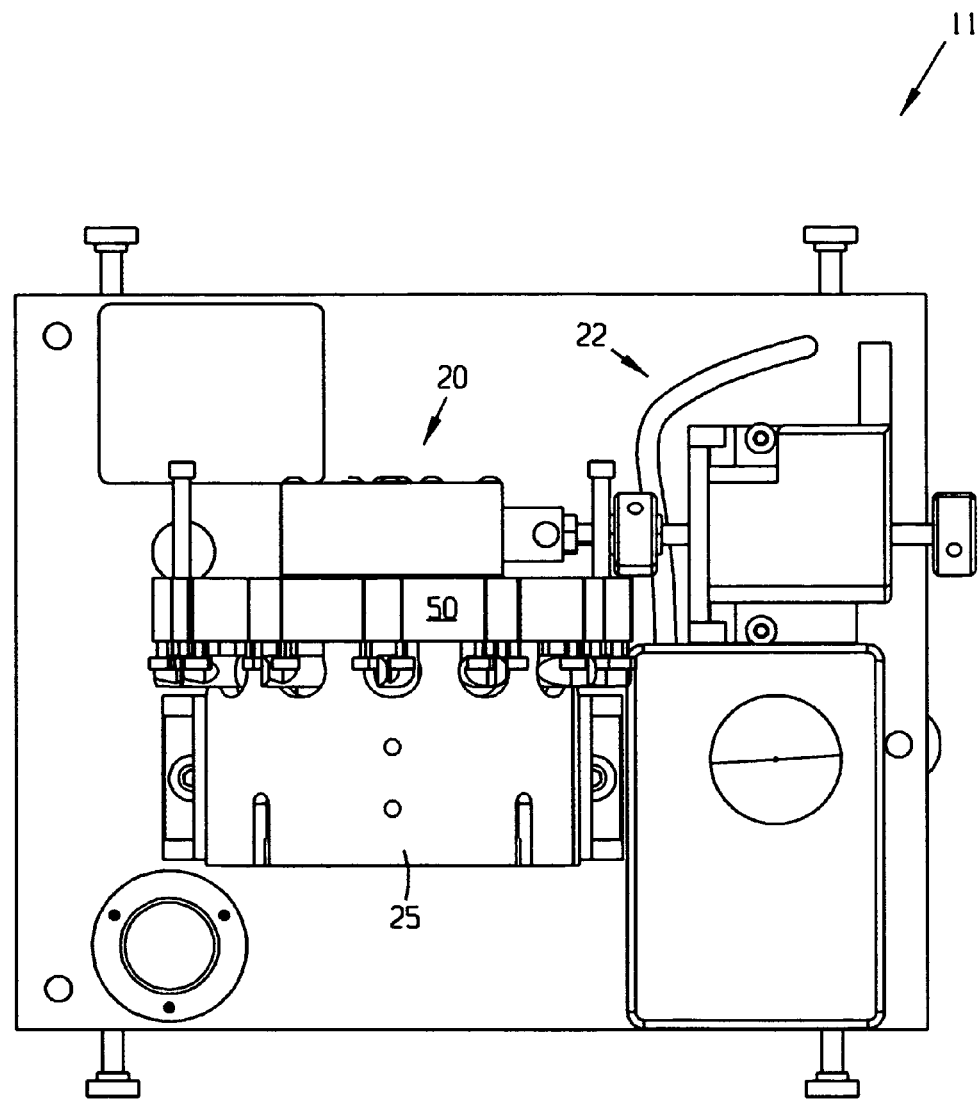
FIGS. 6a/b show a top or plan view of the assembly.
Figure 6B:
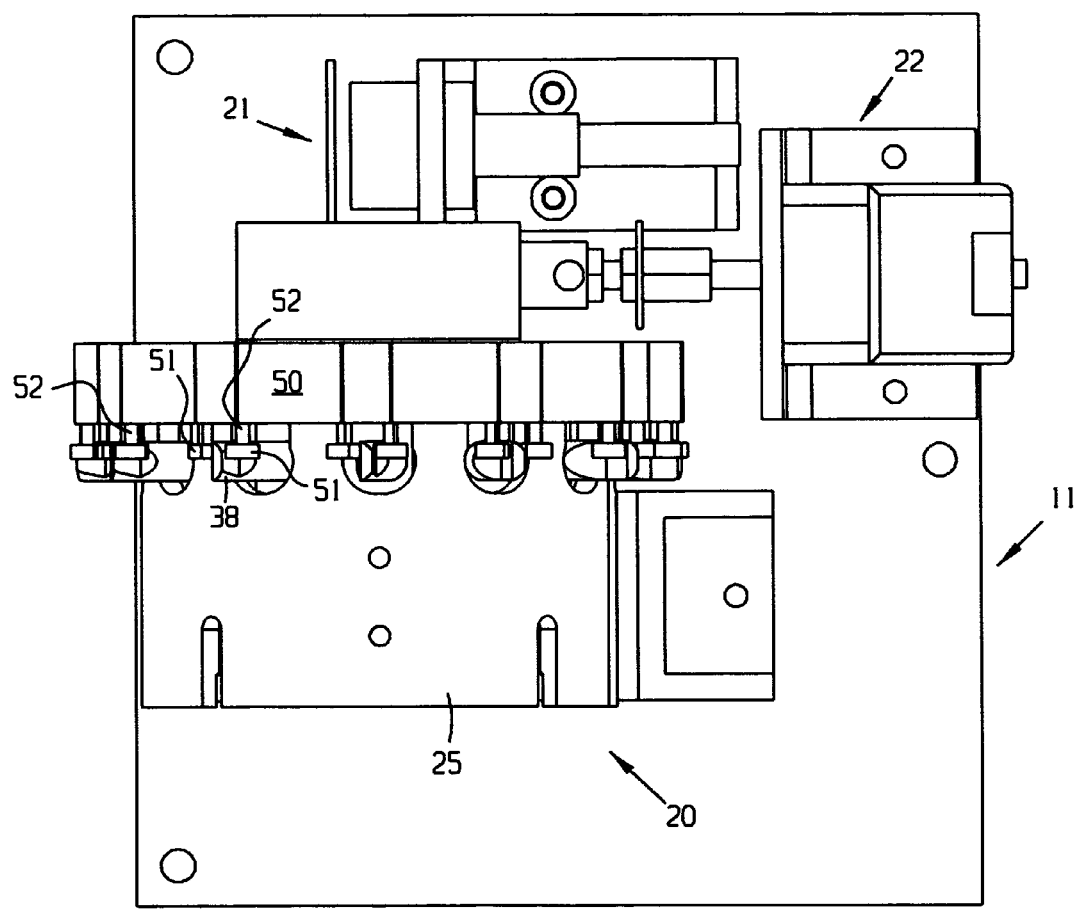
Figure 7:
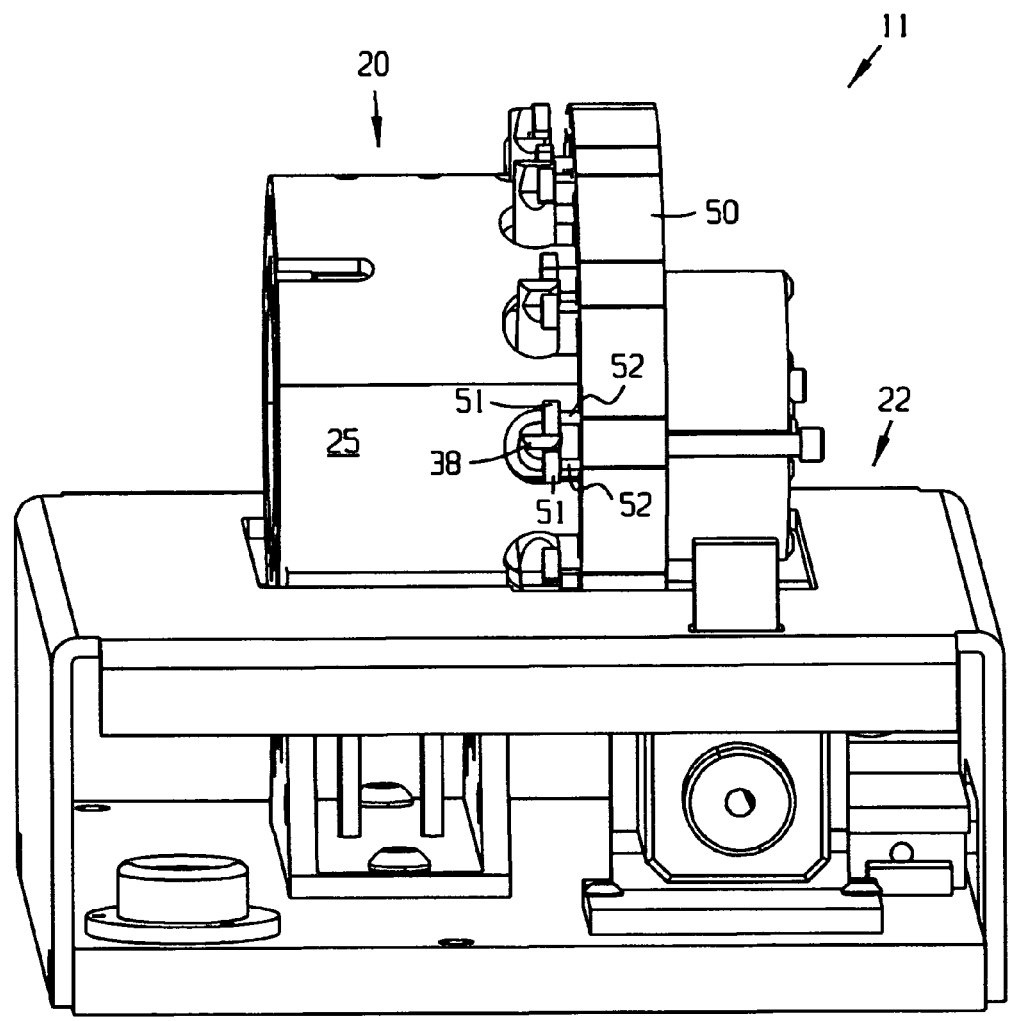
FIG. 7 is a side elevation view of the radial expansion force measurement assembly.
Figure 8:
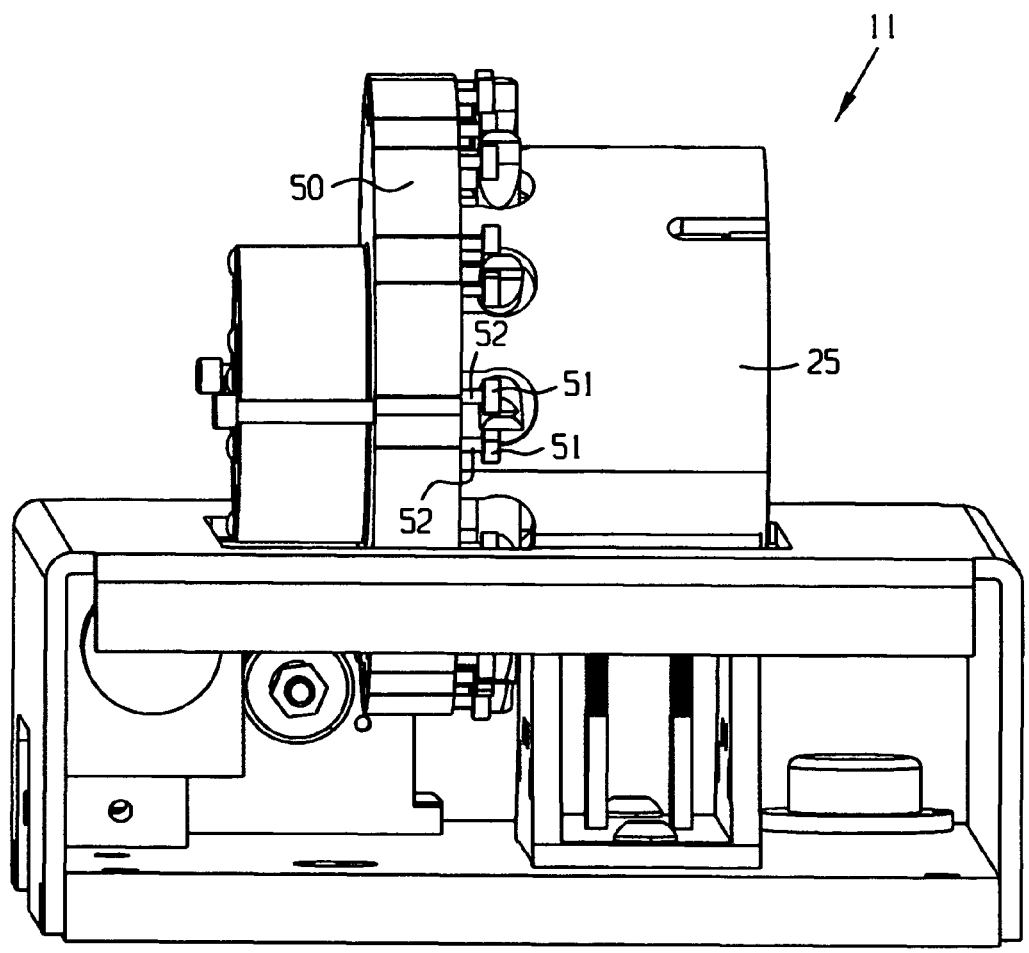
FIG. 8 is an opposing side view of the assembly.
Figure 9:
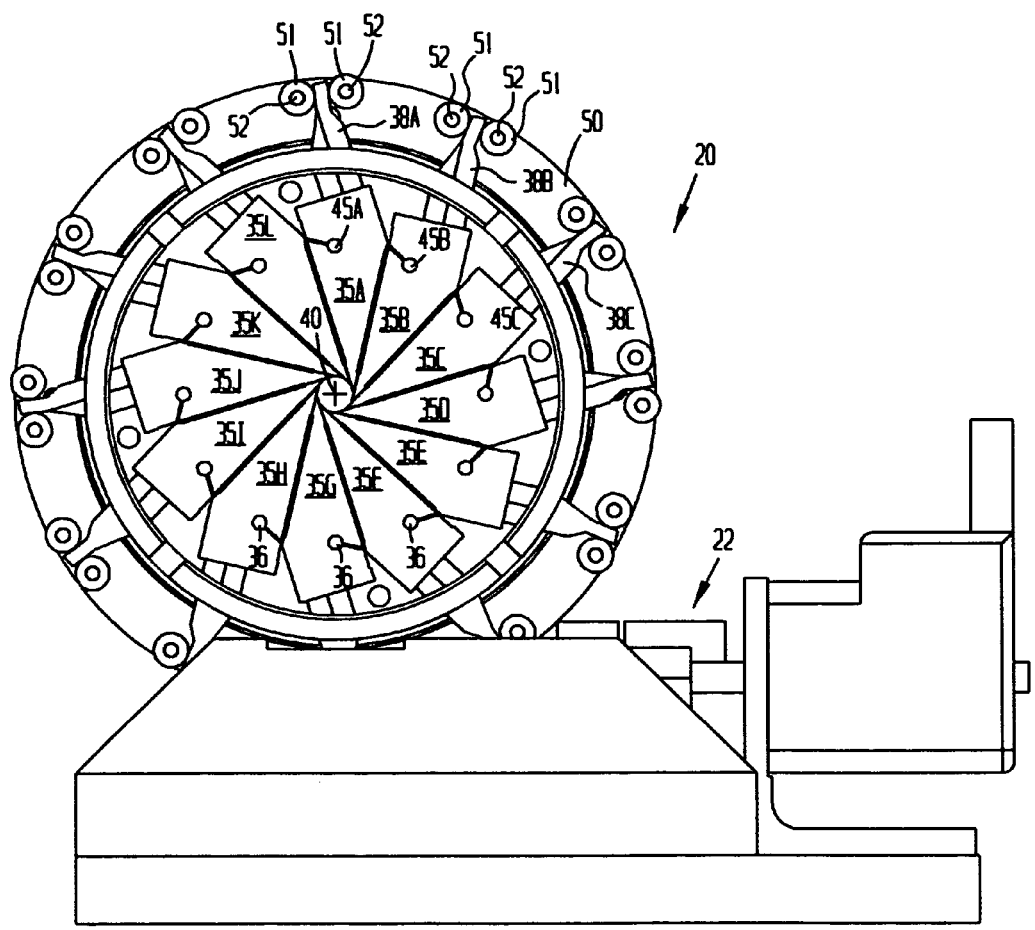
FIG. 9 is a front view of the front face of the radial expansion force measurement assembly, with a front portion removed to show various components.
Figure 10:
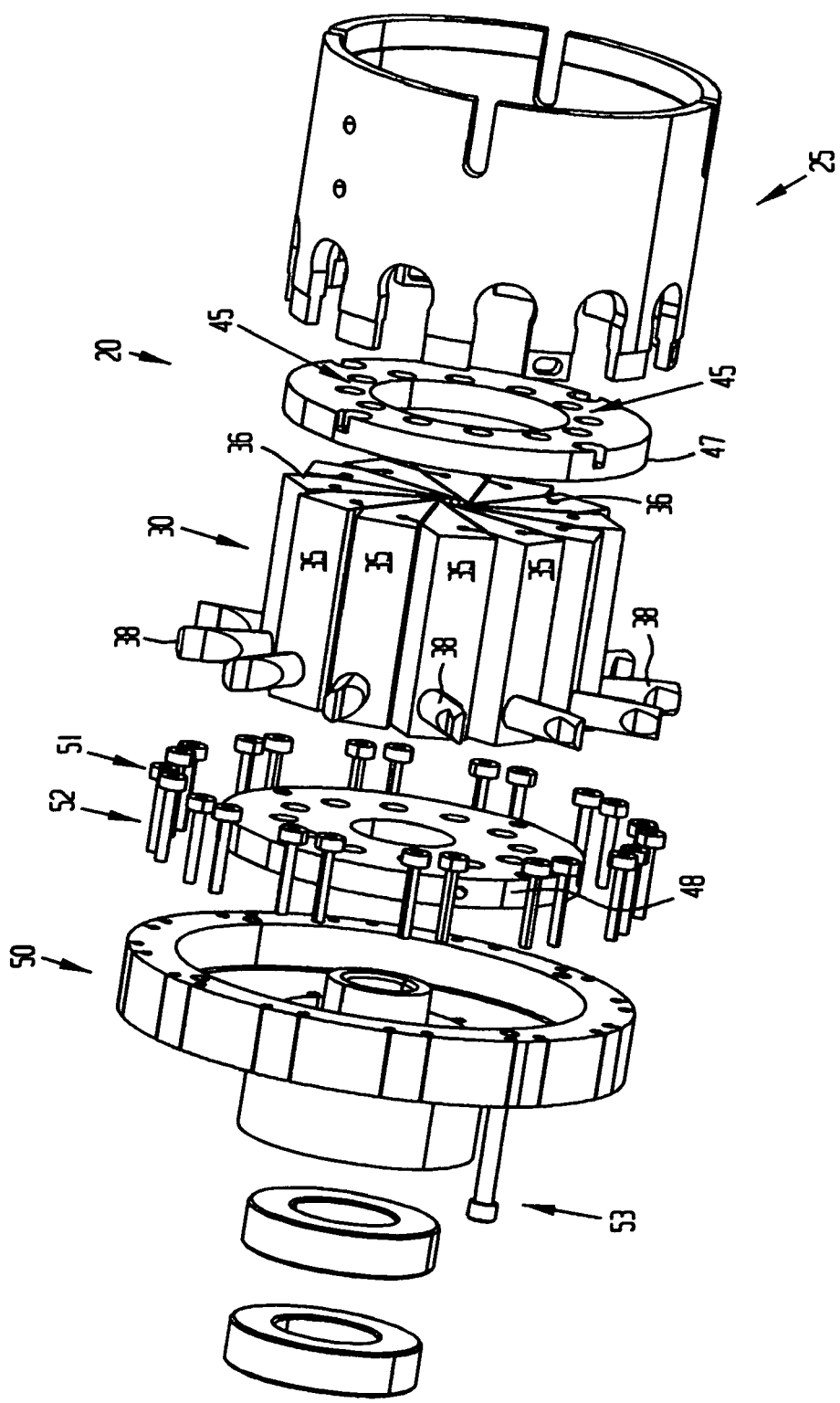
FIG. 10 is an exploded view of the assembly.
Figure 11:
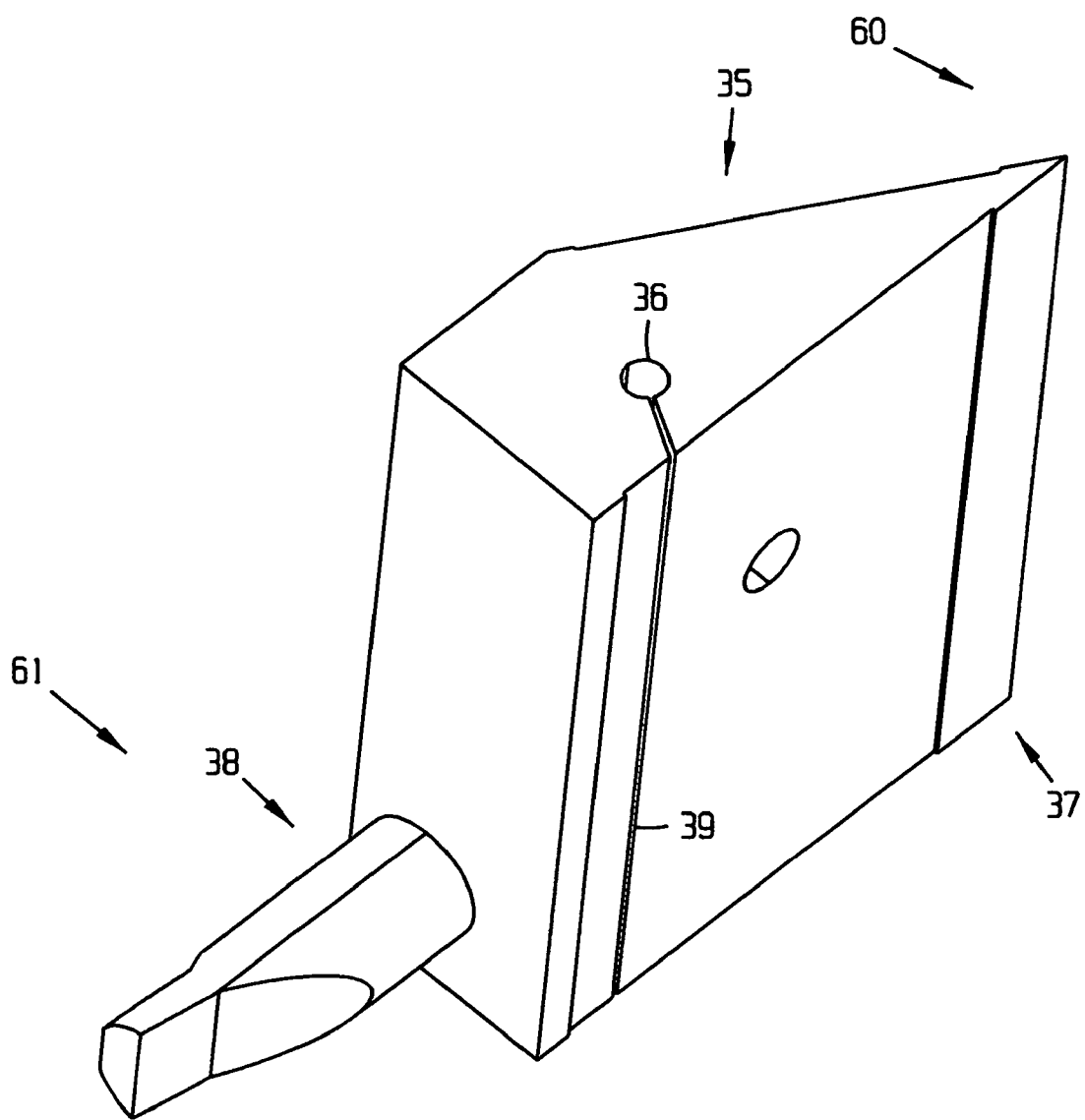
FIG. 11 is a perspective view of an embodiment of a force element of the present invention, which is used in the assembly of FIGS. 1–10.

Referring to FIGS. 1, 12 and 13, the system 10 of the present invention measures the outward force applied by a test specimen, such as a stent 15, to the inside of a substantially circular cylindrical opening formed in a test apparatus 11 head 30. The system 10 is analogous to a typical tensile tester for materials, except that the "extension" and "force" parameters of the tensile tester are replaced by "diameter" and "hoop force" parameters of the present invention. The apparatus 11 measures radially-outward pressure in the circular cylinder 40 much better than known systems, apparatus and methods.

As shown in FIG. 1, an embodiment of the expansion force measurement system 10 of the present invention comprises an expansion force measurement assembly or apparatus 11 communicatively connected to a control module 12. The system 10 is preferably communicatively connected to control software, which is preferably implemented via a microcomputer 13, and most preferably a notebook type PC computer.

Referring to FIGS. 2–10, an embodiment of the expansion force measurement assembly or apparatus 11 of the present invention, which is a part of the system 10, comprises an article engagement mechanism 20, a force transducer 21 such as an optical encoder or load cell, a drive mechanism 22, preferably including a motor and an actuator, all communicatively connected to each other via known electrical and communicative connectors and connection methods. These components are all preferably suitably mounted and housed, by known means, for safety, process efficiency and durability.

Referring in particular to FIGS. 4, 9, 10 and 11, the engagement mechanism 20, comprises a head member 30 which employs a plurality, preferably twelve (12) force elements 35a–l that have a predetermined wedge shaped configuration to form or define a near-cylindrical, substantially circular, longitudinally oriented opening 40 whose cross section is actually a multi-sided (in this case 12 sides) polygon. Each force element 35 has a radially oriented distal end 60 and a proximal end 61. Fixed, cylindrical housing 25 is preferably disposed over head 30 and mounts stationary pin plate 47.

All of the wedge-shaped force elements 35 rotate or pivot freely about distal hinge points 45a–l on pinned ball bearings 46a–l mounted to fixed front and rear (preferably) ring shaped pin plates 47 and 48. Simultaneous rotation of all of the force elements 35 causes the size of the opening 40 to change, including moving inwardly to reduce the diameter of the opening 40 and engage an article 15 located therein. Hinge points 45 are disposed in distally oriented apertures 36 in force elements 35. Such apertures have depending slots 39.

The force elements 35 do not normally substantially touch each other in the head 30 configuration, but the test specimen 15 touches all of the force elements 35. The radially-outward force applied by the specimen to the head opening 40 is divided into 12 forces applied by the specimen 15 onto the distally disposed tip regions 37 of each of the force elements 35.

The apparatus 11 further comprises a rotatable force collector 50, which is preferably a ring that rotates freely about its central axis. The force collector 50 is preferably coincident with the main axis of the head 30 and of the specimen 15. The force collector 50 touches and movably couples a proximally disposed tail member 38a–l of each of the force elements 35 through ball bearing sets 51a–l mounted to the force collector via respective pin sets 52a–l as shown for example in FIG. 10. The ball bearing movable coupling of the tails 38 constrains the force element 35 rotation, and hence the opening 40 diameter, to be a function of the force collector 50 rotation.

Figure 21:
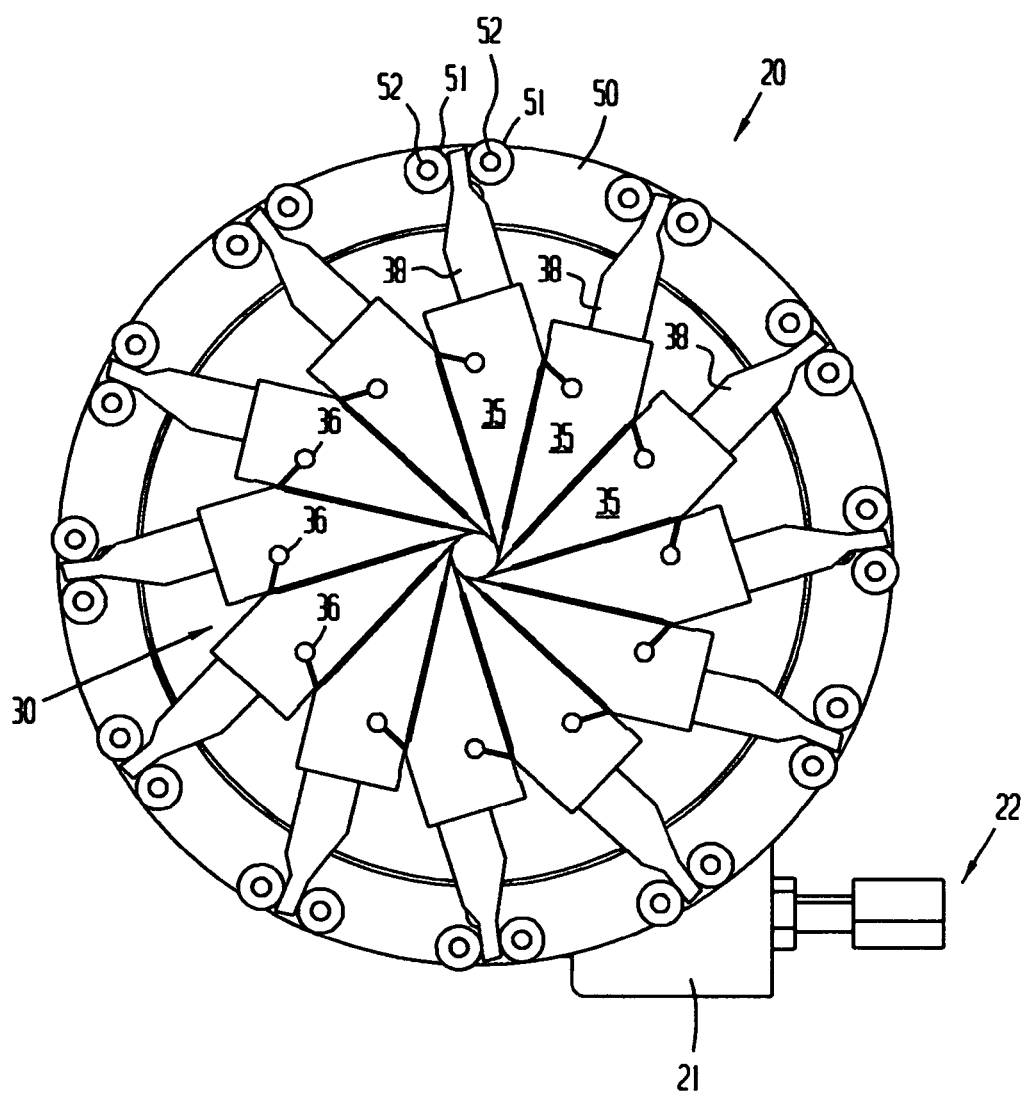
FIG. 21 illustrates an embodiment of the operation of force elements, force collector, force transducer and actuator of the assembly.
Figure 22:
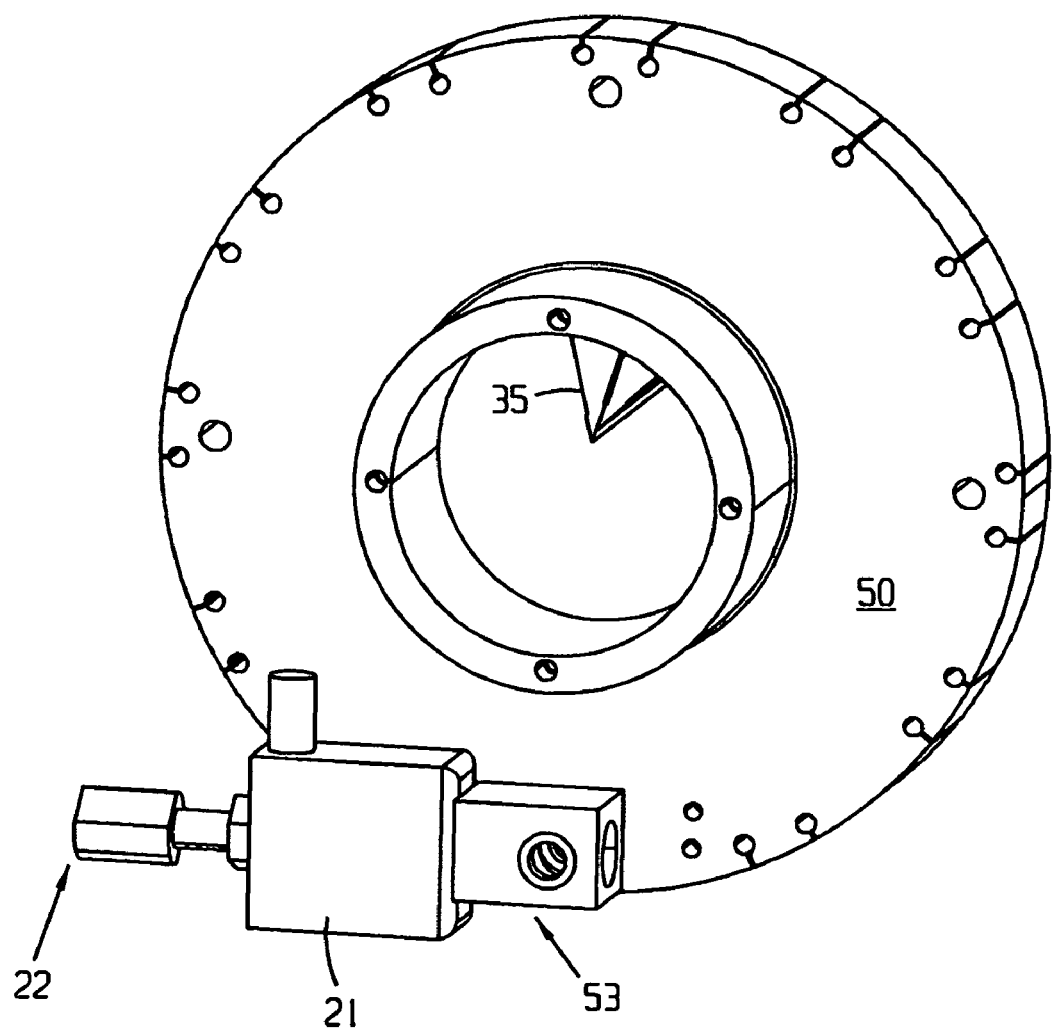
FIG. 22 further illustrates the operation of the elements shown in FIG. 21.

Referring also to FIG. 21, the force collector 50 is attached through another ball bearing attachment assembly 53 to the force transducer 21, which is positioned by the drive mechanism 22. The actuator/motor 22 moves the transducer 21 in the left-right direction with respect to FIG. 21, and hence rotates the force collector. Such movement causes the force elements 35 to move, including to move to reduce the diameter of the central aperture 40 and engage an article therein. The transducer 21 is preferably an optical encoder. It measures the angular rotation of the force collector 50. The encoder 21 transmits pulses to an encoder acquisition board (not shown), which are read by system 10 software. The software uses experimentally determined polynomial curve fits to calculate the opening 40 diameter based on voltage.

In general, the force ($F_N$) on one (1) force element 35 due to pressure (P), along with the friction in the head 30 and head 30 geometry are sensed by the force transducer 21. $F_N$ then is used in a system algorithm along with diameter (D), to calculate hoop force (Hf).

Hoop force is calculated based on:

$$Hf = (P*L*D)/2,$$

where:
L=length
D=diameter and, $$P = (N*F_N)/(\pi*D*L),$$

where N=number of segments

The head 30 provides the near-cylindrical opening 40 whose diameter is controlled to follow a diameter setpoint (constant or a function of time) that the user specifies by interacting via system software. The requested (setpoint) diameter and the measured diameter are continuously displayed. The displayed diameter is that of a circular cylinder tangent to the flat surfaces 37 of the 12 force elements 35, i.e. the size of a gage pin that would just fit in the head 30.

Control and analysis hardware and software are communicatively connected to the article engagement mechanism 11.

In summary, the apparatus 11 comprises:

(a.) an article engagement mechanism 20 having:
  at least one stationary plate member 47/48;
  at least one, and preferably two, rotatable force collector member 50 which is moveable in relation to the at least one stationary member 47/48;
  a plurality of force element segments 35, each having a predetermined wedged shape with a proximal end 61 and a distal end 60, each segment 35 having a distal point 36 and a proximal point 38, the distal point 36 being pivotally coupled (45) to the stationary member 47/48 and the proximal point 38 being movably coupled to the rotatable member 50;
  the segments 35 being arranged so that the segment 35 distal ends 60 are disposed adjacent a central aperture 40; and
  the segment 35 distal ends 60 moving to engage the article 15 upon rotation of the rotatable member 50 in a predetermined direction;

(b.) an actuator 22 for rotating the rotatable member 50; and (c.) a transducer 21 communicatively connected to the actuator 22 for detecting force associated with rotating the rotatable member, and hence engagement of the article 15 by the segment 35 distal ends 60.

3. Principles of Operation

Once again, hoop force in a circular-cylindrical-shell-shaped device, for example a stent as shown in FIGS. 12 and 13, is the total circumferential force transmitted across an imaginary lengthwise cut through the wall of the device. The actual hoop force within test specimen 15 cannot, of course, be measured. The system 10 of this invention measures the force applied by the specimen 15 to multiple sides of a polygon then calculates a hoop-force equivalent.

The principle behind the equivalent of hoop force involves a plurality of relationships relating to diameter and force. Functional relationships for diameter are depicted as:

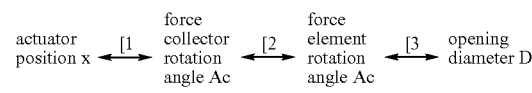

Functional relationships for force are depicted as:

A. Definition of Diameter

Figure 23:
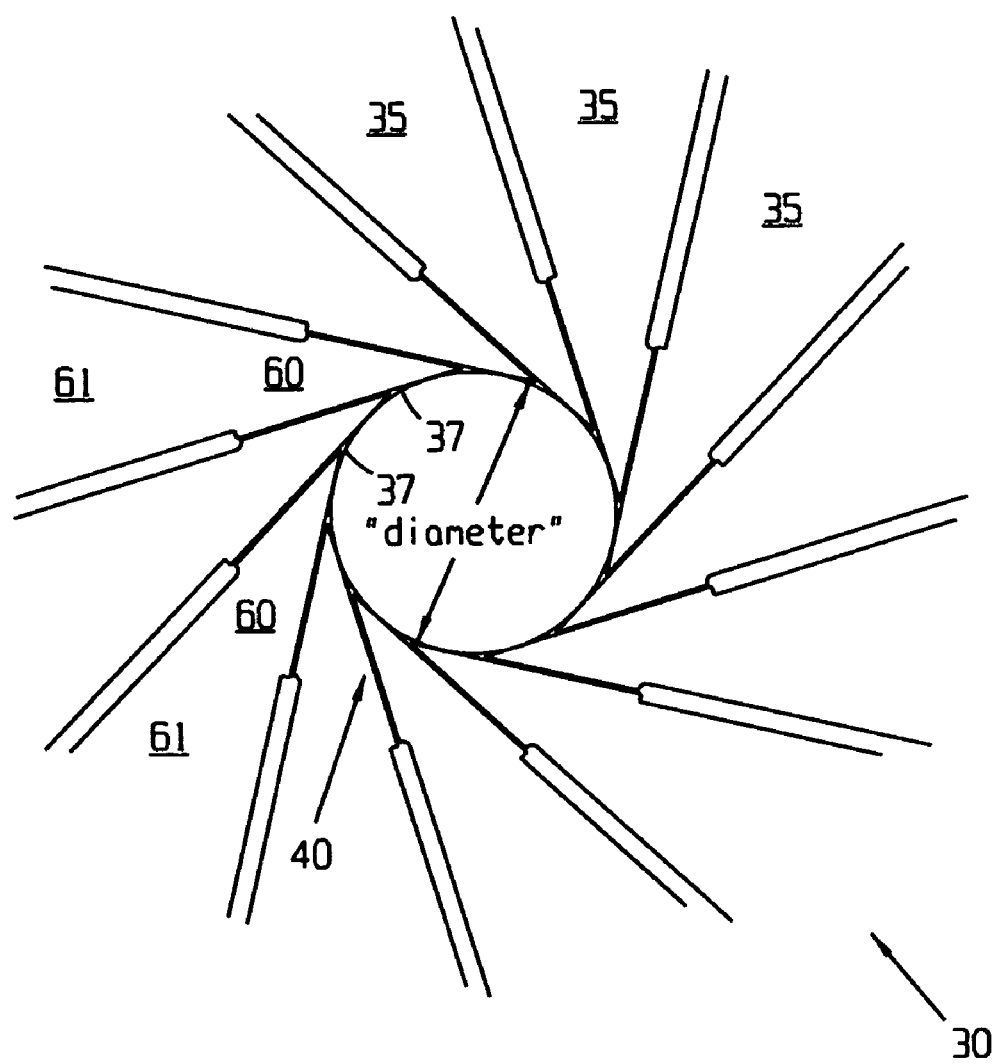
FIG. 23 illustrates an embodiment of the opening diameter of the invention.

Referring also to FIG. 23, the "diameter" of the opening 40 is defined as the diameter of a circular cylinder tangent to the flat surfaces of the 12 force elements 35, i.e. the size of a gage pin that would just fit in the head. The diameter is controlled to follow a diameter setpoint (constant or a function of time) that the user specifies by interacting with the system software.

B. Diameter Relationships

Figure 24:
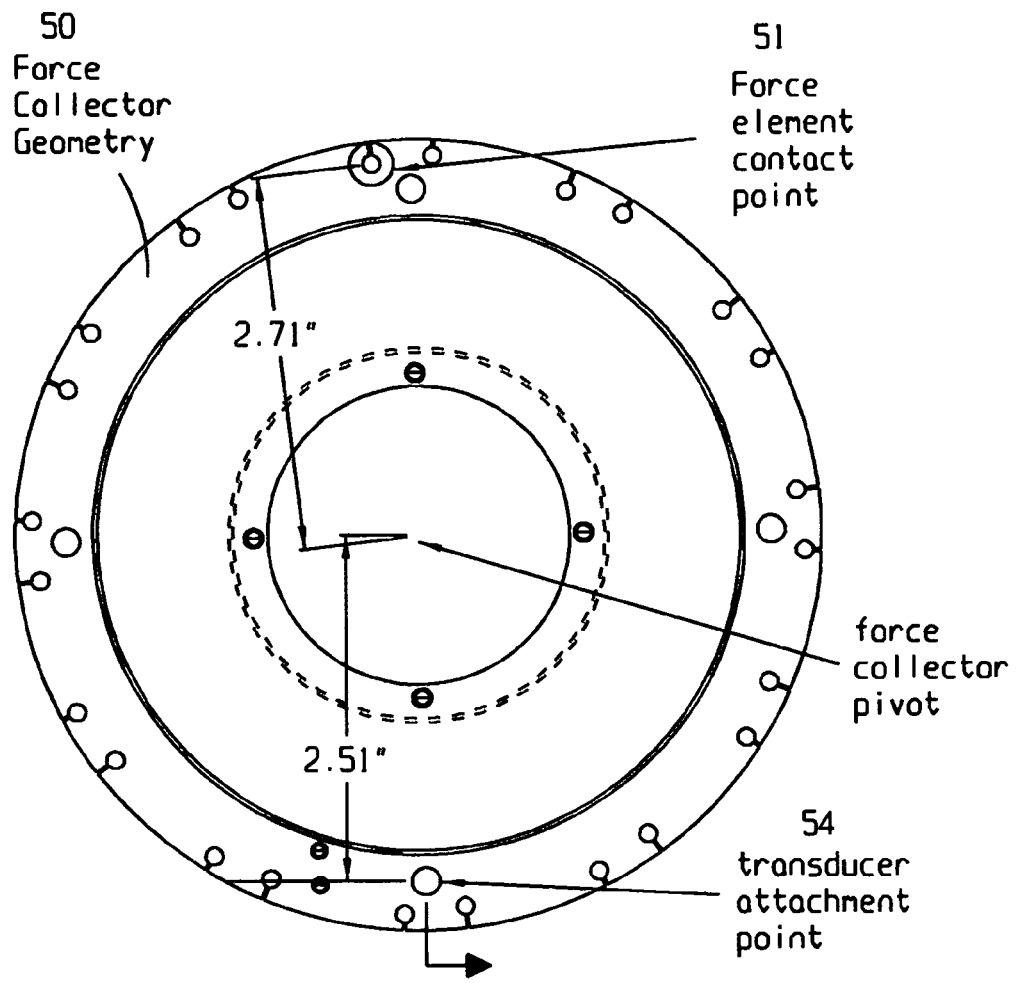
FIG. 24 further illustrates the operation of the assembly, particularly with respect to diameter relationships.

The geometry diagram of the force element 35 and force collector 50 depicted in the drawing Figures are for an apparatus suited to measure test specimens up to about 14 mm in diameter. Referring to FIG. 24, angles are defined such that at a 2.5 mm opening diameter, the rotation angle of the force element is zero, the rotation angle of the force collector is zero, and the stroke of the actuator (or transducer) is zero.

The actuator (or transducer) stroke x causes rotation of the force collector proportional to the distance of the attachment point from the center of rotation (distance=radius×angle). (To use these equations without angle conversions, the angle units must be radians.)

$$Ac = \frac{x}{2.51 \text{ in}} \quad [1]$$

Equating the linear displacement of the ball-bearing contact point between the force collector and the force element gives the second relationship.

$$Ae = \frac{Ac \cdot 2.71 \text{ in}}{1.35 \text{ in}} \quad [2]$$

The change in diameter of the specimen is equal to two times the deflection of the element tip. Deflection of the element tip is the pivot-to-tip distance times the rotation angle.

$$D = 2 \cdot 1.35 \text{in} \cdot Ae + 2.5 \text{ mm} \quad [3]$$

Combining [1], [2], and [3] results in:

$$D = 2.16 \cdot x + 2.5 \text{ mm}$$

C. Specimen Forces

Again, the apparatus 10 cannot measure the actual hoop force within the test specimen 15, but rather measures the force applied by the specimen to the 12 sides of the polygon, then calculates a hoop-force equivalent. Those calculations are approximated by the relationships [4], [5], [6], and [7].

Figure 25:
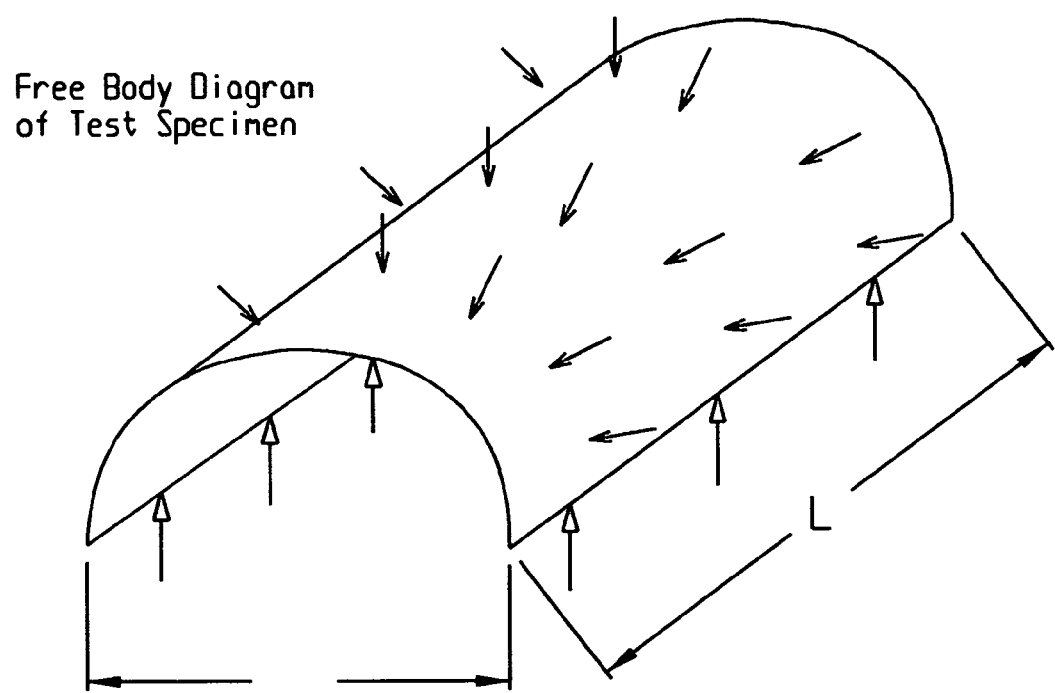
FIG. 25 illustrates the force analysis of the present invention.

For the hoop force/radial force relationship [4], reference is made to the free body diagram of a thin-walled, cylindrical test specimen shown in FIG. 25. The commonly-used definition of "hoop force" in a circular-cylindrical-shell-shaped specimen is the total circumferential force transmitted across an imaginary lengthwise cut through the wall of the device.

Setting the sum of forces in the vertical direction equal to zero results in:

$$HF = \frac{P \cdot L \cdot D}{2}$$

where L is the length of specimen and P is the average pressure exerted on the specimen.

In the apparatus' calculation of hoop force, the diameter D in this relationship is the head opening diameter. The machine cannot use any specimen-dependent diameter such as a mid-wall diameter. However, the user can post-process the data using a spreadsheet to obtain a differently-defined hoop force if desired.

The total radially-outward force RF is defined as the pressure times the surface area.

$$RF = P \cdot \pi \cdot L \cdot D$$

Combining these equations gives the relationship $$RF = 2 \cdot \pi \cdot HF \quad [4]$$

Figure 26:
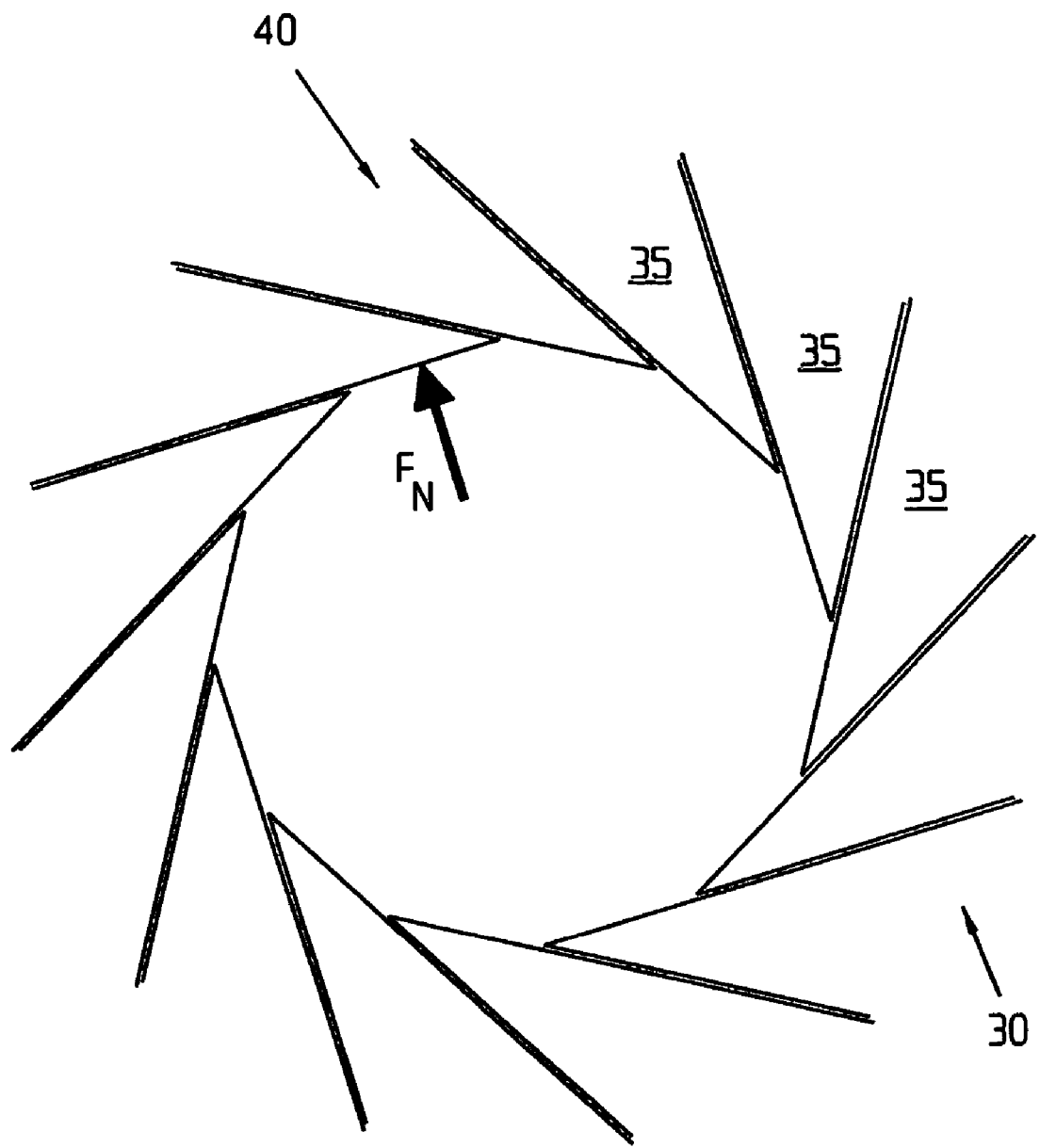
FIG. 26 illustrates an approximation of Fn.

Referring also to FIG. 26, the radial force RF is distributed among the 12 force elements. Fn is defined as the force applied to one element normal to its surface.

$$Fn = RF/N \quad [5],$$

wherein N is the number of force elements, for example twelve, 12.

Here, the location of Fn is approximated at the tip of the element. The location of application of Fn changes slightly with the size of the opening, so that Fn stays in the center of the face of the polygon. Equations [4] and [5] are approximations because the opening is not perfectly round and because there is some friction between the specimen and the force elements.

D. Apparatus Mechanism Forces

Figure 27:
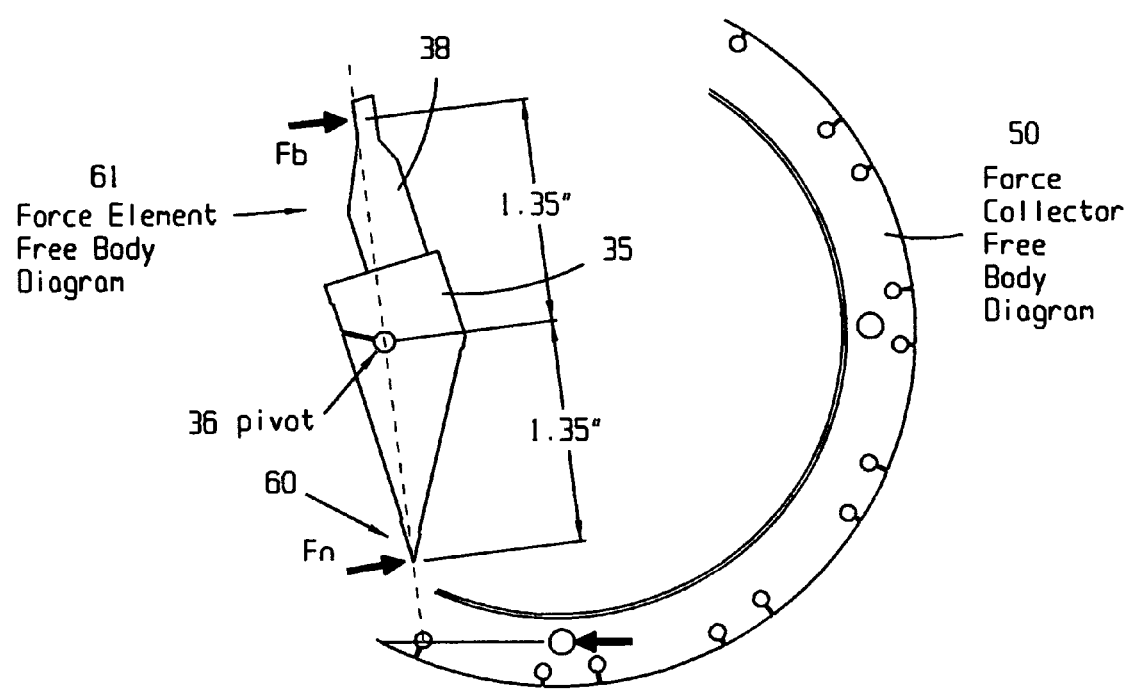
FIG. 27 further illustrates the operation of the assembly, particularly with respect to machine mechanism forces.
Figure 28:
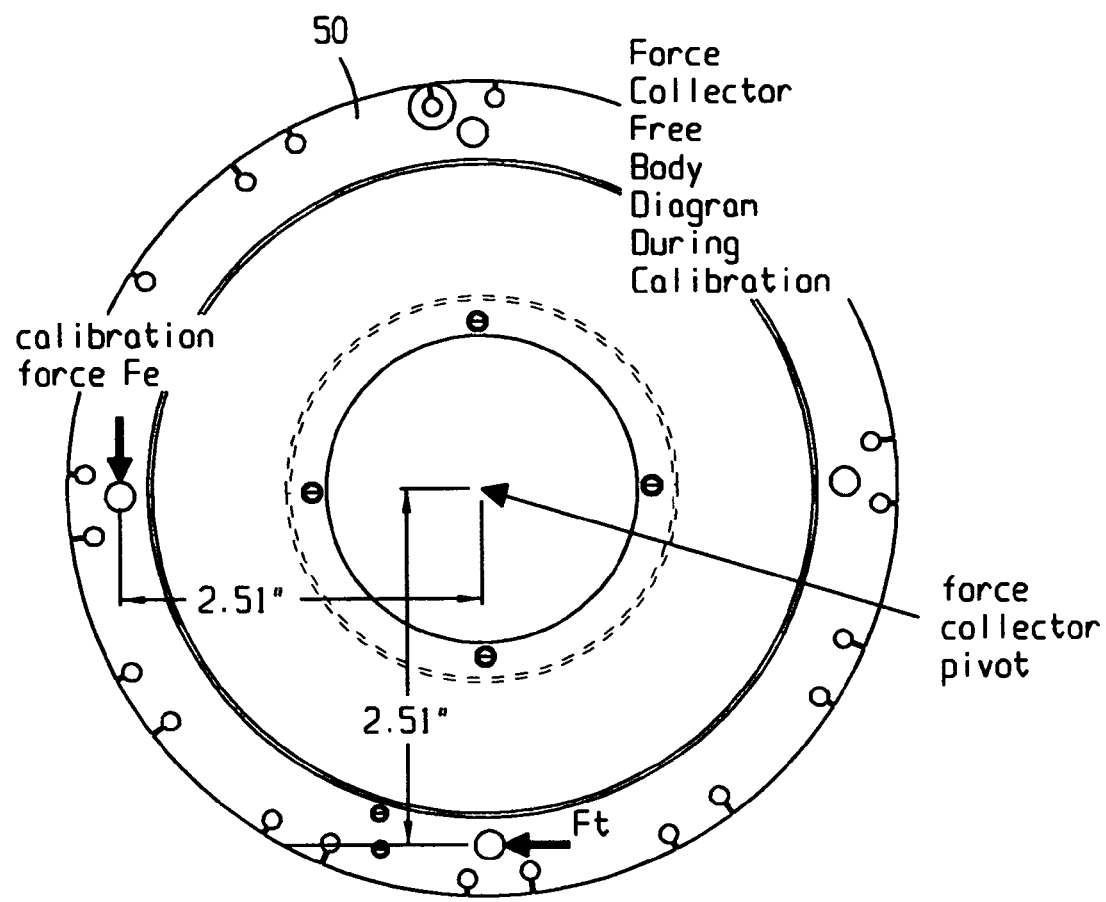
FIG. 28 illustrates assembly forces during a calibration.

Referring to FIG. 27 and to the free body diagrams of the force element and the force collector 50, Fb is the force in the ball bearing at the interface of the force element 35 and the force collector 50. In the force element 35, Fn and Fb cause moments about the pivot that balance each other, resulting in:

$$Fb = Fn \quad [6]$$

Ft is the force applied on the force collector 50 by the transducer 21. This is the force measured by the transducer 21. For the final relationship, Ft and the twelve Fb's cause moments about the center of the force collector that balance each other.

$$Ft = \frac{2.71 \text{ in} \cdot 12 \cdot Fb}{2.51 \text{ in}} \quad [7]$$

Figure 17:
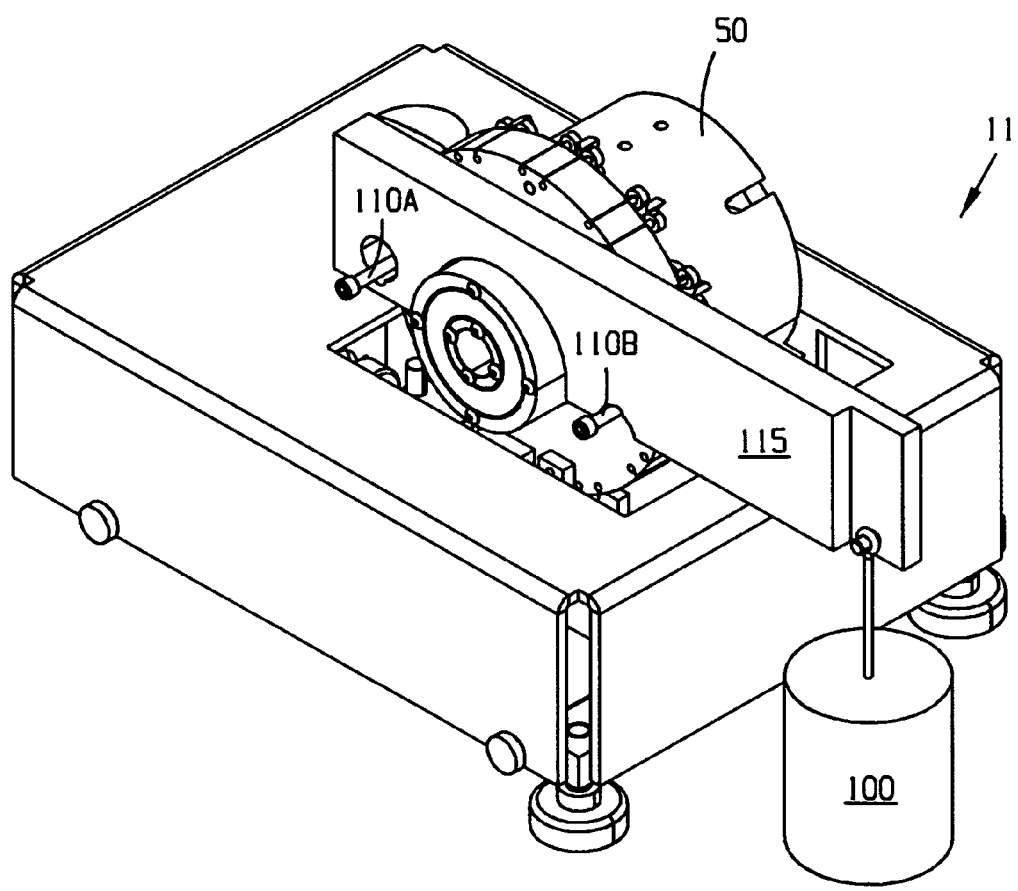
FIG. 17 is a perspective view of an embodiment of the assembly in a calibration setup mode.
Figure 18:
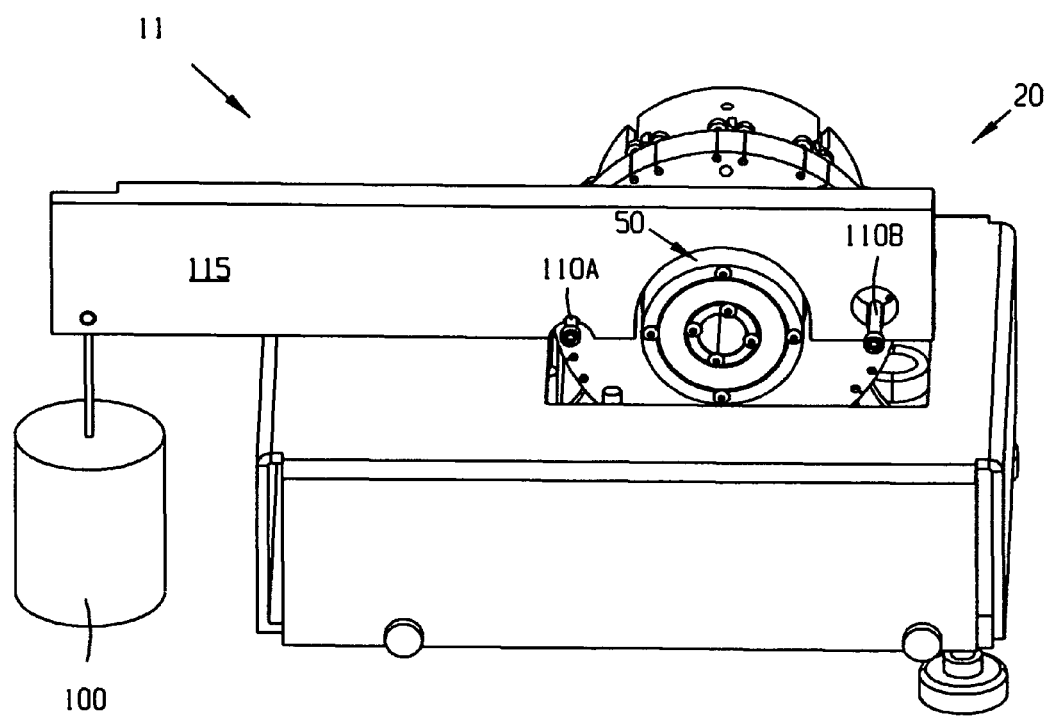
FIG. 18 is another perspective view of the assembly in a the calibration setup mode.

Combining [4], [5], [6], and [7] results in $HF=0.145 \cdot Ft$ or $Ft=6.88 \cdot HF$ $RF=0.926 \cdot Ft$ or $Ft=1.08 \cdot RF$ E. Forces During Calibration Referring to FIGS. 17 and 18, while the force calibration is being performed on the apparatus 11, there is no specimen in the head 30. Instead of specimen forces causing a reading in the transducer 21, a force from a dead weight 100 is applied a shoulder screw 110 on the force collector 50. Reference is made to the free body diagram for calibration.

The moment arm of the calibration (weight) force is the same as the moment arm of the transducer attach point, resulting in:

$Ft=Fc$

Thus, a well-calibrated transducer will read the applied force directly. To achieve higher force levels with reasonably-sized weights, a yoke 115 is supplied with the equipment to multiply the force level of the weights by hanging them with a longer moment arm. The multiplication factor, as well as the force applied by the yoke 115 itself, is marked on the yoke.

F. Relationship of FN to the Force Measured by Force Transducer (Ft)

This functional relationship depends on the geometry of the head 30 mechanism, and is programmed into the system software. The relation varies depending on the machine model and element part number. (A rough approximation for head openings up to about 14 mm in diameter is: Ft=12*FN/0.93, or for head openings up to about 42 mm in diameter: Ft=12*FN/0.98.

$Ft=\text{func}(FN)$

Friction in the head mechanism itself is generally small compared to the measured forces. Typical friction levels in a head of 12 or 14 mm max diameter and 60 mm length are 0.1 lbf of hoop force.

Combining the three relationships described above, the approximate functional relationship of hoop force (HF) to transducer force (Ft) is:

for relatively smaller heads up to 14 mm diameter:

$$HF = \frac{0.93 \cdot Ft}{2 \cdot \pi} \quad \text{or} \quad HF = 0.148 \cdot Ft,$$

and for relatively large heads up to 42 mm diameter:

$$HF = \frac{0.98 \cdot Ft}{2 \cdot \pi} \quad \text{or} \quad HF = 0.156 \cdot Ft$$

System software preferably uses a more exact function that includes higher-order effects in the head geometry model.

It should be taken into account by the user that the actual hoop force in a tested specimen 15 or product likely differs from the displayed "hoop force", potentially significantly, due to the friction between the specimen and the head segments. As the wall of the specimen 15 expands or contracts, it rubs against the 12 rigid planar surfaces of the head 30. The head-to-specimen friction varies depending on the materials and construction of the specimen 15. Although the friction cannot be addressed by the force calibration procedure, it is a systematic and somewhat repeatable effect, and in most cases will not mask differences that are measured among specimens.

The actuation force (Ft) is continuously measured by a strain-gage-type force transducer whose signal-conditioning circuit transmits an analog voltage to the A/D card which is read by the software. Several full-scale force ranges are selectable by changing the force transducer. The software continuously calculates the hoop force from the measured value of Ft. The calculated hoop force is displayed and plotted on the screen, and is stored in a data array for possible writing to a spreadsheet-type (.csv) file.

Other types of expansion force quantities may be calculated by the user. For example, the user may use the spreadsheet to calculate the pressure times length as:

$$P \cdot L = \frac{2 \cdot HF}{D},$$

where HF and D are the hoop force and diameter displayed/written by the RX software. The user can then use a different diameter to calculate a different hoop force. One reason to do this is if the user chooses to use another diameter rather than the head opening diameter in the hoop force calculation.

Another example: The user may choose to use the spreadsheet to calculate the total radial force (pressure times contact area) as follows:

$$RF = \frac{\pi \cdot HF}{2}$$

where RF is the total radial force.

G. Accuracy

Regarding diameter accuracy, the main source of error in the diameter measurement is the variability of the head 30 mechanism geometry. The error is substantially removed by regular calibration using a gage pin. With daily calibration of the diameter, the diameter accuracy can be kept below about ±0.8% of the maximum diameter opening of the head 30. If calibrated just prior to a test, the accuracy is within ±0.4% of the maximum diameter opening. When a single gage pin is measured by the apparatus repeatedly, the standard deviation of the readings is 0.15% of the max head opening or less. The apparatus 11 permits easy calibration. It should be understood that the meaning of "diameter" is of the 12-sided opening 40, as described above. In particular, it should be noted that the perimeter of a 12-sided polygon is 2.35% larger than the circumference of the circle that fits inside the polygon.

Regarding hoop force accuracy, the main consideration is the head-to-specimen 15 friction described above. The sources of error in the rest of the signal path (shown here) are smaller, but include, in approximate order of importance, as follows.

Hoop Force Signal Block Diagram

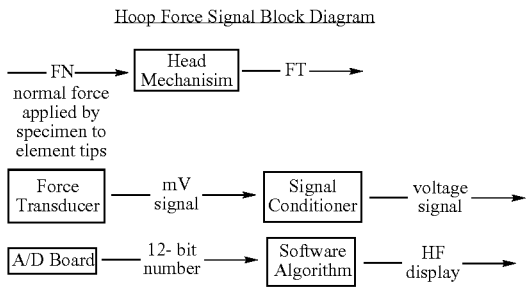

The software algorithm that reconstructs the normal force FN from the transducer force Ft is based on an analytical representation of the head mechanism 30 geometry. We believe that the error in this calculation amounts to less than ±3% of the measured hoop force. This is not addressed by the calibration procedure, but it is a systematic effect that is perfectly repeatable and does not change over time.

The transducer itself is characterized as follows:
 i. nonlinearity: 0.05% of Rated Output
 ii. hysteresis: 0.05% of R.O.
 iii. nonrepeatability: 0.05% of R.O.
 iv. zero balance: 1.0% of R.O.
 v. temp effect on output: 0.005% of load/degF
 vi. temp effect on zero: 0.005% of R.O./degF Items iv, v, and vi are substantially removed by the force calibration procedure.

The analog-to-digital (A/D) circuit board accuracy is approximately ±0.25% of the full scale of the force transducer. The majority of this error is removed by the force calibration procedure.

The force transducer signal conditioning circuit is characterized as follows:
 vii. nonlinearity: 0.01% maximum
 viii. accuracy ±0.05% of FS
 viii. stability ±0.1% for 24 hours The majority of items ii and iii are removed by the force calibration procedure.

The accuracy of the calibration procedure depends on the accuracy of the test weights and the yoke that the weights are hung on. For example, the accuracy of the 14 mm diameter apparatus yoke alone is ±0.015 lbf, and that of the 42 mm diameter apparatus yoke is ±0.025 lbf. The yoke for the smaller apparatus has a moment arm that multiplies the hung weight by 3.0±0.002. The yoke for the larger apparatus has a moment arm that multiplies the hung weight by 4.0±0.003.

For the smaller apparatus:

total force tolerance (+/−)=0.025 lbf+3.0×(tolerance of weights)+0.002×(amount of weights)

For example: A 50 lbf force is applied by hanging a 10±0.001 lbf weight plus a 5±0.0005 lbf weight. Total force tolerance would be plus or minus (0.015 lbf+3×0.0015 lbf+0.002×15 lbf), or ±0.05 lbf, or ±0.1% of full-scale. Since the hoop force is approximately 15% of the transducer force, the hoop force tolerance in this example would be 0.15×0.05 lbf, or ±0.0075 lbf.

H. Resolution

With respect to diameter, resolution of the diameter display are preferably, for 14 mm diameter head: 0.01 mm when using mm units, or 0.01 inches when using inch units; and for 42 mm diameter head: 0.02 mm when using mm units, or 0.02 inches when using inch units. Resolution of the encoder is approximately 0.002 mm of diameter for heads up to 14 mm diameter), and 0.004 mm for heads up to 42 mm diameter.

With respect to force, resolution of the hoop force display is preferably 0.01 N when using N units, or 0.01 lbf when using lbf units. Resolution of the A/D converter for the transducer force signal is approximately 0.06% of the full-scale transducer force. For example, when using a 50 lbf transducer, the resolution of the transducer force is 0.03 lbf. Or, since hoop force is about 15% of transducer force, the resolution of hoop force is 0.0045 lbf.

Alternatively, the article engagement mechanism may be of a general design disclosed in U.S. Pat. No. 6,629,350 to Motsenbocker entitled Stent Crimping Apparatus and Method, which is hereby incorporated by reference.

4. System Operation

Figure 15:
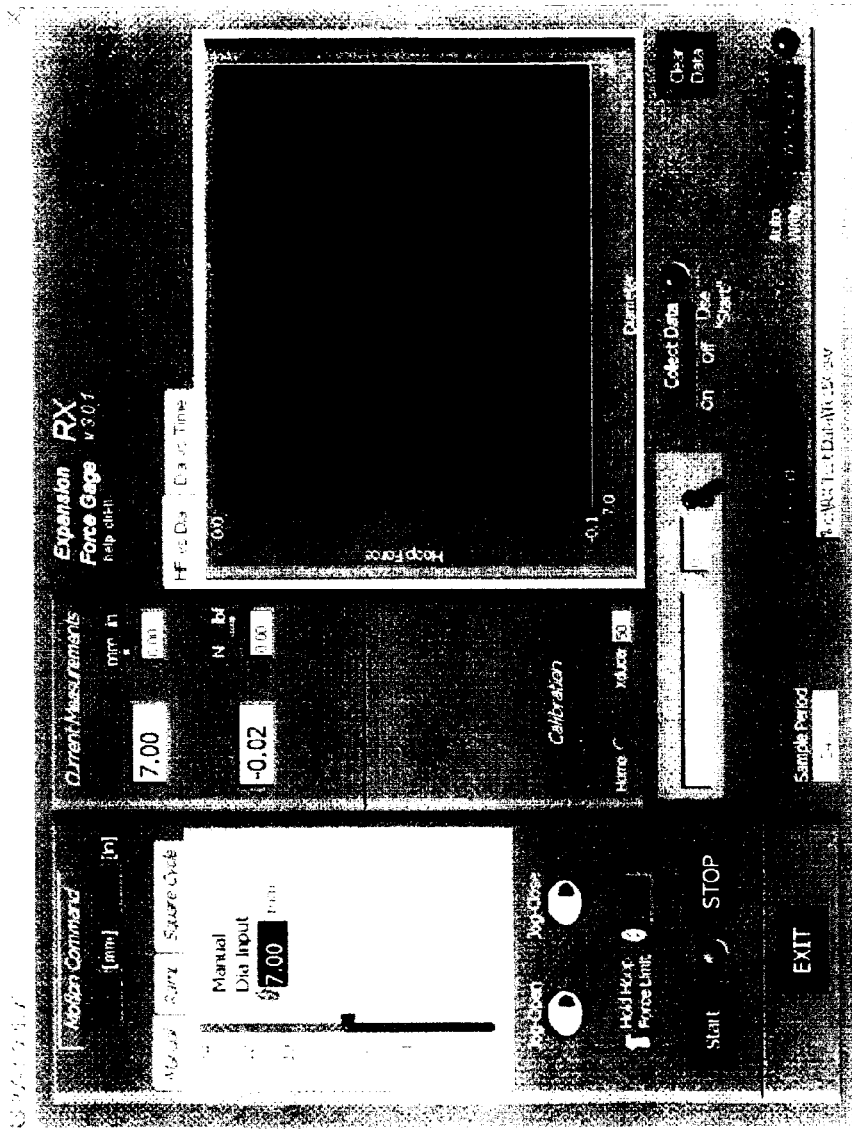
FIG. 15 illustrates an embodiment of a main control screen of an embodiment of the control soft ware of the present invention.

Subsequent to installing, providing power to, and configuring the system, the operator presses ctrl-h at any time to show a context-sensitive help window. Float the cursor over any display or control to show a detailed description. Whether or not the context help window is open, short 'tooltip' descriptions are shown as the mouse floats over all items. Referring to FIG. 15, following a configuration, the main screen is displayed.

A. Control Description

The "Motion Command" portion of the screen is used to control the diameter of the head opening.

Figure 16:
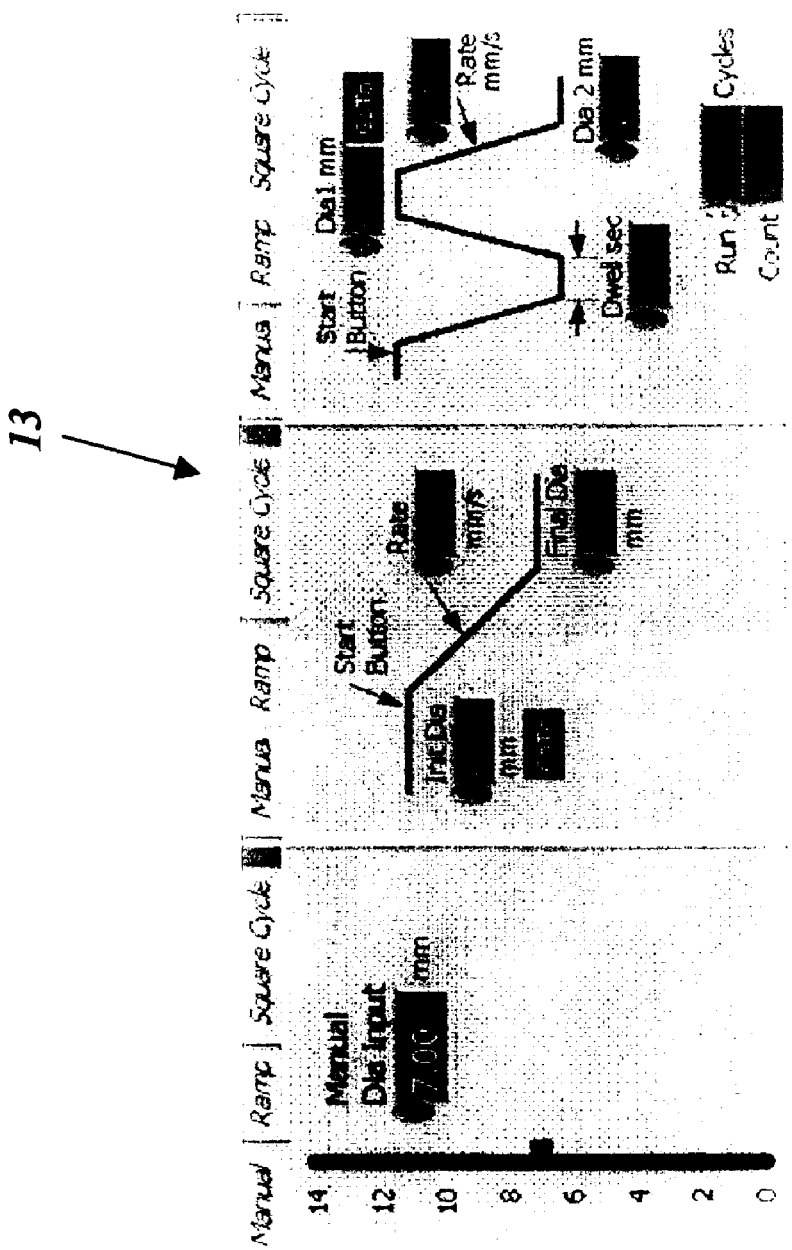
FIG. 16 illustrates an embodiment of a diameter command screen of the control software.

The two displays at the top of FIG. 15 show the current commanded diameter in mm and in inches. The main screen controls comprise:

Dia Input Selection Tabs shown in FIG. 16 are used to selects the type of diameter command: manual, ramp, or cycle:
 Manual:
 Dia Input Manual entry of diameter setpoint, mm. Entry may be by typing, sliding, or clicking on arrows
 Ramp:
 Rate This control allows entry of the rate of change of diameter when Ramp-type diameter command is selected.
 Init Dia This control allows entry of the initial diameter when Ramp-type diameter command is selected. To go to the initial diameter, press the 'GoTo' button.
 Final Dia This control allows entry of the final diameter when Ramp-type diameter command is selected.
 GoTo (Init Dia) This button causes the head to move to the initial diameter, then stop.
 Square Cycle:
 Rate This control allows entry of the rate of change of diameter when the Square Cycle command is selected.
 Dia 2 This control allows entry Diameter 2, one of the two setpoints used when the Square Cycle-type diameter command is selected.
 Dia1 This control allows entry of Diameter 1, one of the two diameter setpoints used when the Square Cycle-type diameter command is selected
 GoTo (Dia1) This button causes the head to move the Diameter 1, then stop.
 Dwell sec This control allows entry of the dwell time at both of the two diameter setpoints when the Square Cycle-type diameter command is selected.

Run This control allows entry of the number of cycles to be run after the "Start" button is pressed. Motion and data collection will stop after these cycles.

Count Displays the current number of completed cycles.

Start/Stop Controls

Start Sends an "enable" command to the motor and begins motion according to the selected motion commands.

Stop The Stop button terminates the motion and disables the motor.

Motion-On Lamp (between Start and Stop buttons) indicates that the motion system is enabled.

Jog Controls

Jog-Close While this button is held down, the head moves in the opening direction. Data is collected during "jog" only if the "Collect Data" control is set to "on".

Jog-Open While this button is held down, the head moves in the closing direction.

Hoop Force Limit Controls

Hold Hoop Force Limit Enables an upper limit to be placed on the hoop force. When the limit is exceeded, a closed-loop controller increases the diameter control setpoint to try to maintain the specified force limit. The force limit control loop is slow; use slow changes in diameter setpoint if overshoot is undesirable.

Hoop Force Limit This control allows entry of the force limit control setpoint. Units are the same as the hoop force display.

The "Current Measurements" portion of the screen is used to continuously display the measurements.

Diameter

Diameter Displays the current measurement of head opening diameter, based on the reading of the encoder.

mm/in Choose units of diameter display, graph, and file output: millimeters or inches.

min Displays the minimum diameter contained in the diameter array (since the array was cleared).

Force

Hoop Force Displays the current measurement of hoop force, based on the measured voltage output of the force sensor signal conditioner.

N/lbf Choose units of hoop force display, graph, & file output: Newtons or Pounds-Force max Displays the maximum Hoop Force contained in the array (since the array was cleared).

The "Data Collection and Graphing" portion of the screen is used to graph the diameter and hoop force measurements, and to control data collection and spreadsheet file writing.

The "Data Collection and Graphing" portion of the screen is used to graph the diameter and hoop force measurements, and to control data collection and spreadsheet file writing.

Graph

Graph Type Use tabs to choose the axes of the graph: Diameter vs. Hoop Force or Time vs. Diameter.

Data Collection

Collect Data Controls collection of data in arrays for graphing and writing to disk: On, Off, or collect data only when "Start" button is pressed. If the "Use Start" button is used, then data collection is stopped when the stop button is pressed or when the preset number of cycles is finished. Data is not collected during use of the "Jog" buttons.

Clear Data Clears the arrays containing time, diameter, and hoop force numbers. (The same arrays are graphed and are written to a spreadsheet disk file.) Any data not yet written to file will be lost.

Sample Period Use pulldown list to select how often the diameter and force data are written to the data array. Applies to both graph and spreadsheet file data.

File Output

File Path This button brings up a file selection dialog to select the spreadsheet file name and location. (Motion must be stopped before the file dialog will run.)

Write to File Write data from arrays (graphed data) to spreadsheet file now. (File Path must already be selected.)

Auto Write When this switch is on (up), the graph data is written to the preselected spreadsheet file automatically each time a square or ramp cycle stops.

SprSh File Display of the file path where the spreadsheet data will be written.

Specimen ID Alpha An alphanumeric entry to identify the test specimen will be written to a header in the spreadsheet file each time the data is written to the file.

(Specimen ID) Numeric A numeric (integer) entry to identify the test specimen will be appended to the alphanumeric entry and written to a header in the spreadsheet file each time data is written to the file.

Auto Inc When this switch is on (up), the numeric part of the specimen identification is automatically incremented each time data is written to the file.

Writing Indicates that data is currently being written to the spreadsheet file.

Collect Data Lamp This lamp indicates that time, diameter, and hoop force numbers are currently being stored in arrays that are graphed in real time and can later be written to a spreadsheet file.

Other Controls and Indicators

Diameter Calibration This button brings up a screen used to calibrate the diameter measurement. (Motion must be stopped before the diameter calibration will run.)

Force Calibration This button brings up a screen used to calibrate the force measurement. (Motion must be stopped before the force calibration will run.)

Home This button opens the screen to allow the encoder to find the reference mark. (The homing routine is normally run automatically whenever the program is started and the reference mark has been lost due to powering down the control module. But this button allows the homing routine to be run manually.)

Xducer Displays the capacity of the installed force transducer in lbf. To change, restart the program and use the dialog box.

E-Stop or No Power Lamp indicates no main power to the motor; E-stop button is pressed or main power to control module is switched off or disconnected.

Exit Disables the motor/controller then terminates the program.

B. Specimen Testing Procedure

An example test procedure follows machine installation, connection, startup and calibration for a user.

1. Note the identity of the sample to be tested and enter it in the "Specimen ID Alpha" field. (Optionally, a numeric portion of the specimen ID may be entered, so that the numeric part may be automatically incremented between tests to speed up testing of large numbers of samples.)

2. Select the "Square Cycle" motion command tab. Enter the upper and lower diameters of the desired cycle. Enter the ramp rate, period, and number of cycles to be run.
3. Press the "GoTo" button to move the head to the initial diameter.
4. Insert the specimen fully into the head opening. (This assumes the initial diameter is larger than the specimen; if not, hold down the "Jog Open" until the specimen fits, then press "GoTo" again.)
5. Use the "File Path" button to enter a file name for data to be written to the disk.
6. Press the "Clear Data" button to clear the arrays containing diameter and hoop force data. Slide the "Collect Data" selector to the "Use Start" position. Select the "HF vs Dia" tab of the graph.
7. Press the "Start" button and allow the machine to run the specified cycles. Watch the data in real time on the graph, which is continuously auto-scaled to show all the data in the arrays.
8. When the cycles are finished, press the "Write Data" button. The data that was shown on the graph is written to the previously-specified disk file.
9. Press the "Exit" button to exit the system software, then use a spreadsheet program to view, process, or graph the data.

The method of detecting force associated with an article comprises the steps of:
a. providing an article engagement mechanism 20 having:
   at least one, and preferably two, stationary pin plate member 47/48;
   at least one rotatable force connector member 50 which is moveable in relation to the stationary member 47/48;
   a plurality of segments 35, each having a proximal end 61 and a distal end 60, each segment 35 having a distal point 36 and a proximal point 38, the distal point 36 being pivotally coupled (45) to the stationary member 47/48 and the proximal point 38 being pivotally coupled to the rotatable force collector member 50;
   the segments 35 being arranged so that the segment 35 distal ends 60 are disposed adjacent a central aperture 40; and
   the segment 35 distal ends 60 moving to reduce the diameter of Th the central aperture 40, and thus engage any article disposed therein, upon rotation of the rotatable force collector member 50 in a predetermined direction;
b. placing an article 15 in the central aperture 40;
c. applying an engaging force to the article 15 with the distal ends 60 of the segments 35 by rotating the force collector 50; and
d. measuring the force required to rotate the force collector 50 and engage the article 15.

C. Calibration Procedure

Referring again to FIGS. 17 and 18, calibration is done in two steps, first with respect to diameter, and then with respect to force. If the force reading is far out of calibration, then the steps should be as to force, then diameter, then force. The force adjustment is a physical, hardware adjustment. The diameter offset and gain adjustments are saved in a file on the computer hard disk. The "Find Home" routine does not need to be run prior to calibration. But if the "Find Home" routine was run, then best accuracy will achieved if diameter is calibrated subsequently.

First, place the machine base near the edge of a solid tabletop so that weights hung from the yoke can hang below the table surface. Level the base using the bubble level. To adjust, screw the feet into or out of the base plate. The bubble should approximately align with the circle on the level.

Diameter calibration involves two steps: 1) offset adjustment and 2) gain adjustment. The offset is adjusted using a small $1^{st}$ gage pin. The optional gain adjustment uses a larger, $2^{nd}$ gage pin, and does not need to be done as often. The diameters of the two gage pins depend on the part number of the force elements. The calibration screen automatically specifies the correct gage pin sizes, depending on the element part number that was entered by the user when the program was started. (Do not insert any pins yet.)

For force calibration, a force level must be chosen. The total calibration force normally should be equal to, or a large fraction of, the capacity of the transducer. During calibration, the actual force signal from the transducer is displayed. The transducer force is not the same as the hoop force. For most normal force levels, the calibration yoke is used. The yoke itself is made so that it applies a known force to the transducer. The yoke force level is marked on the yoke (5.0 lbf for RX500, 15.0 lbf for RX600). Any weights hung on the yoke show up at the transducer as a multiplier times the actual weight the multiplier is marked on the yoke (3× for 14 mm head, 5× for 42 mm head). For example, if a 50 lbf transducer is used on an 14 mm machine, the yoke plus a 5-lbf and a 10-lbf weight would normally be used. (5 lbf for the yoke plus 3×5 plus 3×10 equals 50 lbf). Weights have top and bottom hooks, and be strung together vertically.

To calibrate to low force levels, the customer may choose to hang weights directly on one of the shoulder screws (#1 for 14 mm head or #2 for 42 mm). It is placed so that any weight hung directly on it equals the force on the transducer 21. A hole in the base is provided to allow a hanging string to pass through and hang below the edge of a table. On the 14 mm head 30, there is also an additional tapped hole in the base for a leveling foot allowing a direct-hanging weight to hang over the edge of a support table.

Figure 19:
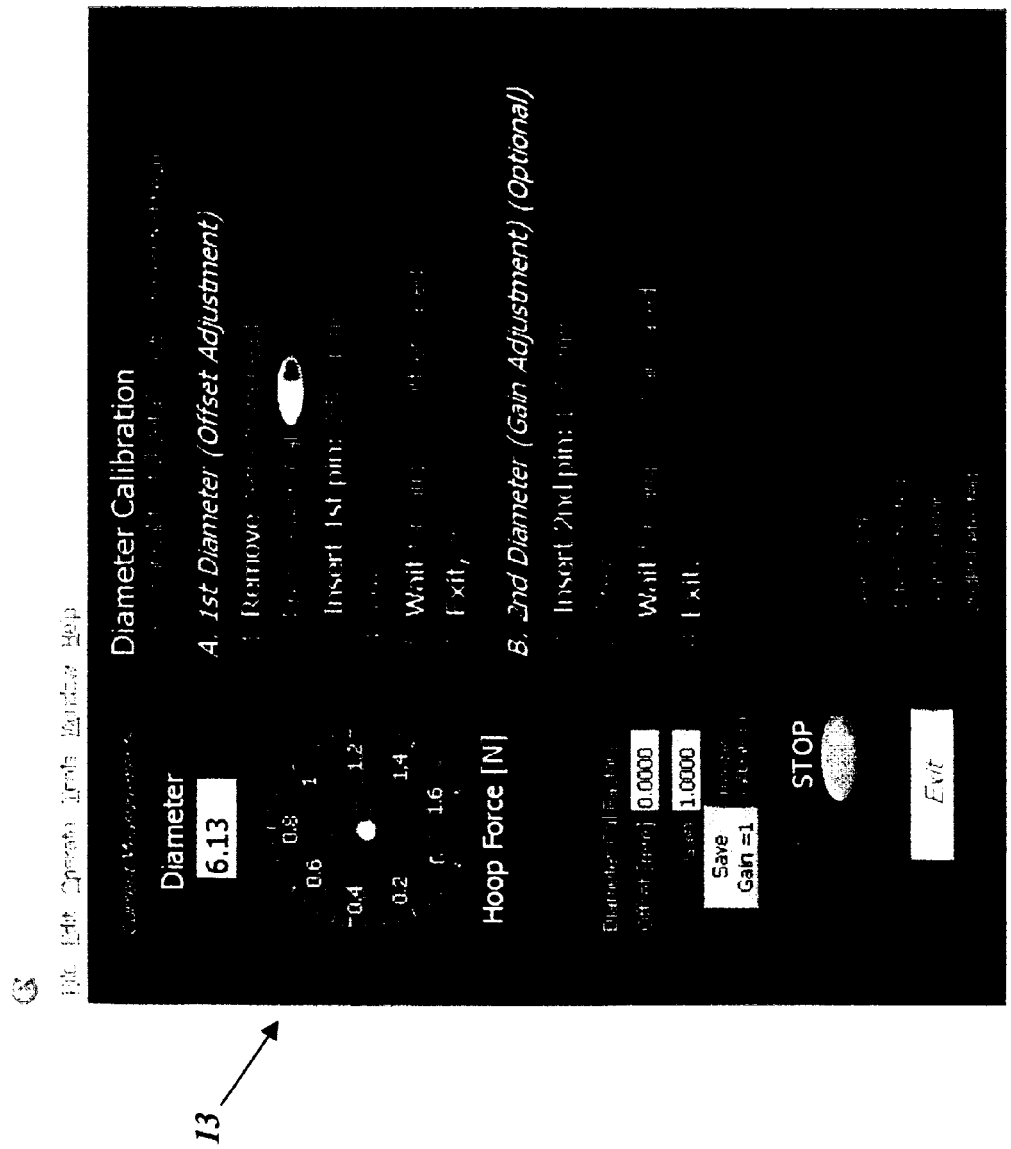
FIG. 19 illustrates an embodiment of a diameter calibration screen of the control software.
Figure 20:
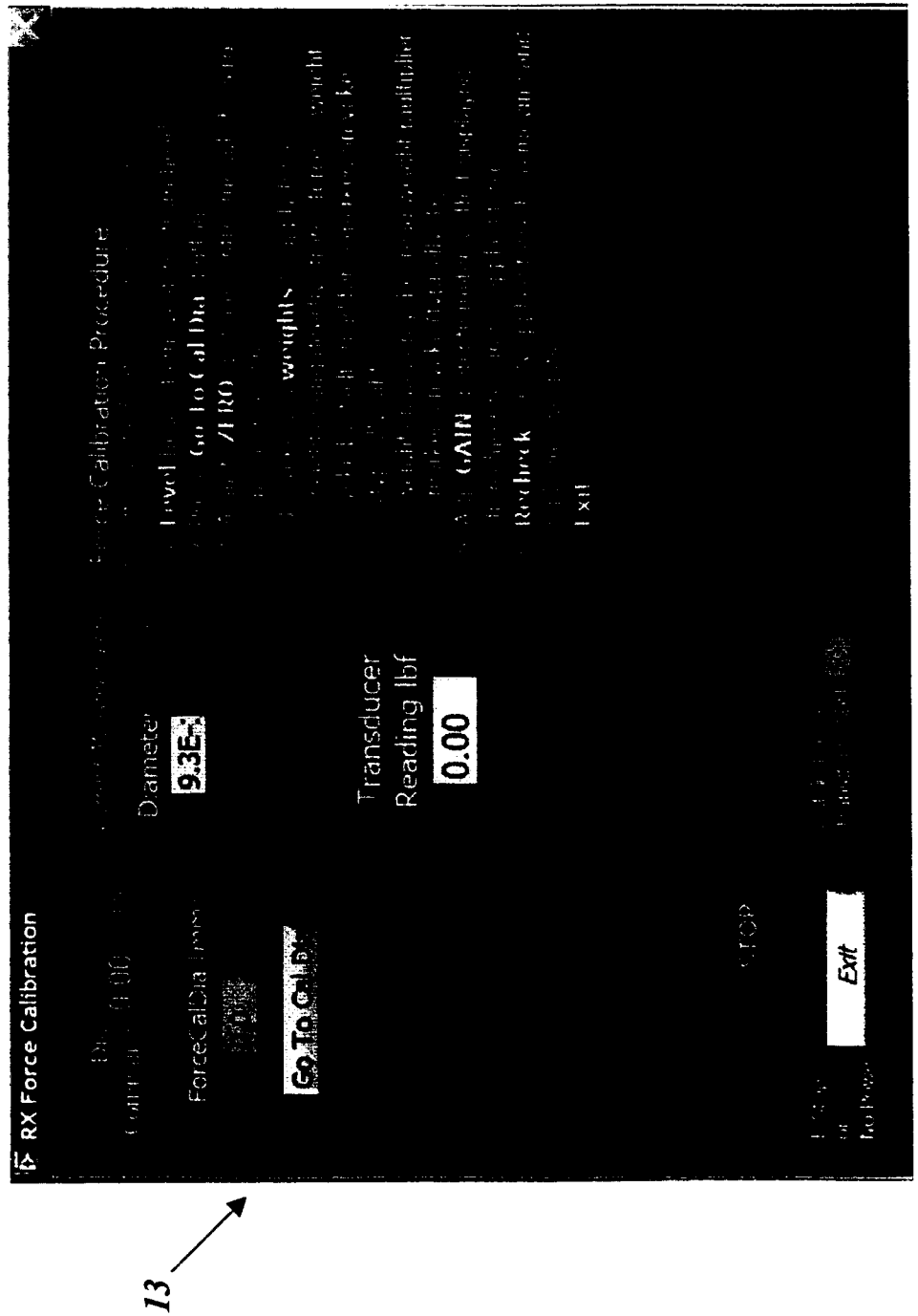
FIG. 20 illustrates an embodiment of a force calibration screen of the control software.

Referring also to FIGS. 19 and 20, subsequent to the calibration preparation steps discussed above, the following calibration procedure is performed:
1. Start up the software. At the opening configuration dialog, check that the physical identity of the force transducer and force elements match the software display. Prior to running the diameter calibration, check that the hoop force level reads around zero (+−1.0 N or so) when nothing is in the head; if not, then run the force calibration first.
2. Diameter Calibration
   a. At the main screen, press the "Diameter Calibration" button. The system Diameter Calibration screen is displayed. The "$1^{st}$ Cal Dia" and "$2^{nd}$ Cal Dia" indicators show the diameters of the gage pins that will be used. (Do not insert pins yet.)
   b. With NOTHING in the head, press the "Begin Cal" button on the calibration screen.
   c. Insert most of the length of the 1st gage pin in the head (at least 1.5 inches). Use great care when inserting steel gage pins so that force elements are not scratched or damaged.
   d. Press the "Cal on $1^{st}$ Pin" button.
   e. The head closes slowly until the hoop force rises due to contact with the pin. When the pin is sensed, the offset value is saved and the "offset saved" lamp comes on. The head 30 opens to release the pin.

f. Remove the 1<sup>st</sup> gage pin.

g. The zeroing portion of the diameter calibration is now finished. The following steps show the procedure for the optional gain adjustment. The gain adjustment has a very small effect. The "Dia Gain Factor" display shows the current gain factor that is in use. If desired, the gain adjustment may be skipped by pressing the "Exit" button; in this case the gain adjustment from the last calibration will be retained. Or, the "Save Gain=1" button may be pressed, canceling the use of a gain adjustment altogether.

h. Insert the 2<sup>nd</sup>, larger gage pin into the head 30.

i. Press the "Cal on 2<sup>nd</sup> Pin" button. The head closes slowly and senses the pin. When the pin is sensed, the gain value is saved and the "Gain Saved" lamp comes on.

j. Remove the 2nd gage pin.

k. The offset and gain factors are actually written from RAM to the computer's disk when the "Exit" button is pressed, so be sure to use the "Exit" button to terminate the diameter calibration screen.

Optionally, to check the diameter calibration at any time, use the manual diameter command on the main software screen. Enter a diameter command and press the start button. Insert any gage pin in the head, then slowly, in 0.01 mm increments, reduce the diameter command until the head touches the pin, as signified by the hoop force rising above 1.0 Newtons. Read the MEASURED diameter (not the command) and compare to the gage pin diameter.

2. Force Calibration a. From the main screen, press the "Force Calibration" button to enter the force calibration screen.

b. Press the "Go To Cal Dia" button to level the shoulder screws. After the head reaches the correct diameter, the "Transducer Reading" is displayed.

c. Use a flat blade screwdriver to adjust the "ZERO" potentiometer on the back of the control module (FIG. 11) so that the "Transducer Reading" is as close as possible to 0.0.

d. Apply the calibration force using the weights and/or yoke. Adjust the "GAIN" potentiometer on the back of the control module (FIG. 11) so that the "Transducer Force" is as close as possible to the applied force.

e. Remove the applied force and recheck the zero. If necessary, adjust the ZERO and GAIN pots again. Press the "EXIT" button to return to the main screen.

The benefits of the invention include, but are not necessarily limited to:

1. Measurement, display and recording of Hoop Force vs. Diameter and Hf per Length vs. Diameter.
2. Low specimen to fixture friction.
3. Low pinching forces.
4. High repeatability, reproducibility, accuracy, and resolution.
5. Easy to use with decreased set up time, simplified data acquisition, easy calibration and low maintenance.

The descriptions above and the accompanying materials should be interpreted in the illustrative and not the limited sense. While the invention has been disclosed in connection with the preferred embodiment or embodiments thereof, it should be understood that there may be other embodiments which fall within the scope of the invention.

The invention claimed is:

1. An apparatus for detecting force associated with an article, comprising:
    (a.) an article engagement mechanism having:
        at least one stationary member;
        at least one rotatable member which is moveable in relation to the stationary member;
        a plurality of segments, each having a predetermined shape with a proximal end and a distal end, each segment having a distal point and a proximal point, the distal point being pivotally coupled to the stationary member and the proximal point being movably coupled to the rotatable member;
        the segments being arranged so that the segment distal ends are disposed adjacent a central aperture; and
        the segment distal ends moving to engage an article disposed in the central aperture upon rotation of the rotatable member in a predetermined direction;
    (b.) an actuator for rotating the rotatable member; and
    (c.) a transducer communicatively connected to the actuator for detecting force associated with rotating the rotatable member.

2. The apparatus of claim 1, wherein the article engagement mechanism is a segmental radial engagement mechanism and the force being measured is hoop strength of a stent.

3. The apparatus of claim 1, comprising two stationary members, each member being disposed at opposing longitudinally disposed ends of the segments.

4. The apparatus of claim 1, wherein the stationary member has a plate-like, ring shaped configuration with a central aperture.

5. The apparatus of claim 1, wherein the stationary member has a plurality of apertures disposed at predetermined locations for receiving longitudinally oriented pivotal connection members which couple with the segments.

6. The apparatus of claim 5, wherein the pivotal connection members include a bearing.

7. The apparatus of claim 1, wherein the stationary member is connected to a fixed housing.

8. The apparatus of claim 1, wherein the rotatable member is a force collector.

9. The apparatus of claim 1, wherein the rotatable member has a cylindrical configuration with a longitudinally disposed member which is rotatably coupled to the stationary member.

10. The apparatus of claim 1, wherein the rotatable member has a plurality of apertures disposed at predetermined locations for receiving longitudinally oriented pivotal connection members which couple with the segments.

11. The apparatus of claim 9, wherein the connection members include at least one bearing.

12. The apparatus of claim 11, wherein the connection members include two bearings disposed to slidably restrain movement of the proximal point of a segment.

13. The apparatus of claim 1, wherein the rotatable member is connected to the transducer at a predetermined point, and wherein the transducer is connected to the actuator, whereby the transducer measures force exerted by the actuator to rotate the rotatable member.

14. The apparatus of claim 1, wherein each segment is radially oriented with respect to the central aperture, along a line between a distal end of the segment to the proximal end of the segment.

15. The apparatus of claim 1, wherein each segment has a longitudinally oriented pivot aperture disposed at the distal point for longitudinally oriented pivotal connection members which couple with the stationary member.

16. The apparatus of claim 1, wherein each segment has a radially oriented tail member disposed at the proximal point, the tail being movably coupled to the rotatable member, whereby rotation of the rotatable member causes the segment to pivot about the distal point.

17. The apparatus of claim 16, wherein each tail member is coupled to the rotatable member by a bearing.

18. The apparatus of claim 1, further comprising a logic system for converting the force detected by the transducer to radial expansion force of an article disposed in the central aperture.

19. The apparatus of claim 18, wherein the logic system converts transducer force to radial expansion force via:

$$Hf=(P*L*D)/2,$$

where:
Hf=radial expansion force
L=length
D=diameter
and, $$P=(N*F_N)/(\pi*D*L),$$

where
N=number of segments
$F_N$=force applied to one element normal to its surface.

20. An apparatus for detecting radial expansion force associated with a stent, comprising:
(a.) a segmental radial article engagement mechanism having:
two stationary plate members;
one rotatable force collector member which is moveable in relation to the stationary plate members and disposed on one side of one member;
a plurality of force element segments, disposed between the stationary plate members, each having a predetermined wedge shape with a radially oriented proximal end and a distal end, each segment having a distal point and a proximal point, the distal point being pivotally coupled to the stationary plate members and the proximal point being movably coupled to the rotatable force collector member;
the force element segments being arranged so that the segment distal ends are disposed adjacent a central aperture which is adapted to receive the stent; and
the force element segment distal ends moving to engage the stent disposed in the central aperture upon rotation of the rotatable force collector member in a predetermined direction;
(b.) an optical encoder communicatively connected to the rotatable force collector member for detecting force associated with rotating the rotatable member; and
(c.) an actuator for rotating the rotatable member via the optical encoder physical connection.

21. A method of detecting force associated with an article comprising the steps of:
a. providing an article engagement mechanism having:
at least one stationary member;
at least one rotatable member which is moveable in relation to the stationary member;
a plurality of segments, each having a proximal end and a distal end, each segment having a distal point and a proximal point, the distal point being pivotally coupled to the stationary member, and the proximal point being movably coupled to the rotatable member;
the segments being arranged so that the segment distal ends are disposed adjacent a central aperture; and
the segment distal ends moving to reduce the diameter of the central aperture upon rotation of the rotatable member in a predetermined direction;
b. placing an article in the central aperture;
c. rotating the rotatable member; and
d. measuring the force required to rotate the rotatable member.

22. An apparatus for detecting force associated with an article, comprising:
(a.) an article engagement mechanism having:
two stationary members;
at least one rotatable member which is moveable in relation to the stationary member;
a plurality of segments, each having a predetermined shape with a proximal end and a distal end, each segment having a distal point and a proximal point, the distal point being pivotally coupled to the stationary member and the proximal point being movably coupled to the rotatable member; each stationary member further being disposed at opposing longitudinally disposed ends of the segments;
the segments being arranged so that the segment distal ends are disposed adjacent a central aperture; and
the segment distal ends moving to engage an article disposed in the central aperture upon rotation of the rotatable member in a predetermined direction;
(b.) an actuator for rotating the rotatable member; and
(c.) a transducer communicatively connected to the actuator for detecting force associated with rotating the rotatable member.

23. An apparatus for detecting force associated with an article, comprising:
(a.) an article engagement mechanism having:
at least one stationary member connected to a fixed housing;
at least one rotatable member which is moveable in relation to the stationary member;
a plurality of segments, each having a predetermined shape with a proximal end and a distal end, each segment having a distal point and a proximal point, the distal point being pivotally coupled to the stationary member and the proximal point being movably coupled to the rotatable member;
the segments being arranged so that the segment distal ends are disposed adjacent a central aperture; and
the segment distal ends moving to engage an article disposed in the central aperture upon rotation of the rotatable member in a predetermined direction;
(b.) an actuator for rotating the rotatable member; and
(c.) a transducer communicatively connected to the actuatQr for detecting force associated with rotating the rotatable member.

24. An apparatus for detecting force associated with an article, comprising:
(a.) an article engagement mechanism having:
at least one stationary member;
at least one rotatable force collector member which is moveable in relation to the stationary member;
a plurality of segments, each having a predetermined shape with a proximal end and a distal end, each segment having a distal point and a proximal point, the distal point being pivotally coupled to the stationary member and the proximal point being movably coupled to the rotatable member;

the segments being arranged so that the segment distal ends are disposed adjacent a central aperture; and the segment distal ends moving to engage an article disposed in the central aperture upon rotation of the rotatable member in a predetermined direction;

(b.) an actuator for rotating the rotatable member; and (c.) a transducer communicatively connected to the actuator for detecting force associated with rotating the rotatable member.

25. An apparatus for detecting force associated with an article, comprising:

(a.) an article engagement mechanism having:

at least one stationary member;

at least one rotatable member which is moveable in relation to the stationary member;

a plurality of segments, each having a predetermined shape with a proximal end and a distal end, each segment having a distal point and a proximal point, the distal point being pivotally coupled to the stationary member and the proximal point being movably coupled to the rotatable member, each segment further having a radially oriented tail member disposed at the proximal point, the tail being movably coupled to the rotatable member, whereby rotation of the rotatable member causes the segment to pivot about the distal point;

the segments being arranged so that the segment distal ends are disposed adjacent a central aperture; and the segment distal ends moving to engage an article disposed in the central aperture upon rotation of the rotatable member in a predetermined direction;

(b.) an actuator for rotating the rotatable member; and (c.) a transducer communicatively connected to the actuator for detecting force associated with rotating the rotatable member.

26. An apparatus for detecting force associated with an article, comprising:

(a.) an article engagement mechanism having:

at least one stationary member;

at least one rotatable member which is moveable in relation to the stationary member;

a plurality of segments, each having a predetermined shape with a proximal end and a distal end, each segment having a distal point and a proximal point, the distal point being pivotally coupled to the stationary member and the proximal point being movably coupled to the rotatable member;

the segments being arranged so that the segment distal ends are disposed adjacent a central aperture; and the segment distal ends moving to engage an article disposed in the central aperture upon rotation of the rotatable member in a predetermined direction;

(b.) an actuator for rotating the rotatable member;

(c.) a transducer communicatively connected to the actuator for detecting force associated with rotating the rotatable member; and (d) a logic system for converting the force detected by the transducer to radial expansion force of an article disposed in the central aperture; the logic system converting transducer force to radial expansion force via:

$$Hf = (P * L * D)/2,$$

where:
 Hf=radial expansion force
 L=length
 D=diameter
and, $$P = (N * F_N)/(\pi * D * L),$$

where
 N=number of segments
 $F_N$=force applied to one element normal to its surface.

* * * * *